(12) United States Patent
Gerber

(10) Patent No.: US 7,097,825 B2
(45) Date of Patent: Aug. 29, 2006

(54) METHODS AND REAGENTS TO ACQUIRE MRI SIGNALS AND IMAGES

(75) Inventor: Michael Gerber, Denver, CO (US)

(73) Assignee: Allos Therapeutics, Inc., Westminster, CO (US)

( * ) Notice: Subject to any disclaimer, the term of this patent is extended or adjusted under 35 U.S.C. 154(b) by 663 days.

(21) Appl. No.: 10/082,130

(22) Filed: Feb. 25, 2002

(65) Prior Publication Data

US 2003/0017612 A1 Jan. 23, 2003

Related U.S. Application Data

(60) Provisional application No. 60/271,237, filed on Feb. 23, 2001.

(51) Int. Cl.
A61B 5/055 (2006.01)

(52) U.S. Cl. .................. 424/9.3; 424/9.33

(58) Field of Classification Search ............. 424/9.3, 424/9.32, 9.33, 9.36, 9.37; 600/410, 420; 436/173
See application file for complete search history.

(56) References Cited

U.S. PATENT DOCUMENTS

| | | |
|---|---|---|
| 5,049,695 A | 9/1991 | Abraham et al. |
| 5,122,539 A | 6/1992 | Abraham et al. |
| 5,248,785 A | 9/1993 | Abraham et al. |
| 5,250,701 A | 10/1993 | Abraham et al. |
| 5,290,803 A | 3/1994 | Abraham et al. |
| 5,382,680 A | 1/1995 | Abraham et al. |
| 5,432,191 A | 7/1995 | Abraham et al. |
| 5,525,630 A | 6/1996 | Hoffman |
| 5,591,892 A | 1/1997 | Abraham et al. |
| 5,648,375 A | 7/1997 | Abraham |
| 5,650,156 A | 7/1997 | Grinstaff et al. |
| 5,661,182 A | 8/1997 | Abraham et al. |
| 5,677,330 A | 10/1997 | Abraham et al. |
| 5,705,521 A | 1/1998 | Abraham |
| 5,731,454 A | 3/1998 | Abraham et al. |
| 5,765,562 A | 6/1998 | Lekunbach et al. |
| 5,827,888 A | 10/1998 | Abraham et al. |
| 5,927,283 A | 7/1999 | Abraham et al. |

FOREIGN PATENT DOCUMENTS

| | | |
|---|---|---|
| WO | WO 97/34594 | 3/1997 |
| WO | WO 01/14316 | 3/2001 |

OTHER PUBLICATIONS

Abraham et al. (1992) *Biochem.* 31:9141-9149.
Abraham et al. (1998) *Med. Chem. Res.* 8:478-486.
Burke et al. (2001) *Kidney Intl.* 60:1407-1414.
Curtis et al. (1997) *J. Appl. Physiol.* 83:1681-1689.
Doppenberg et al. (1997) *Annals. of the N.Y. Acad. of Sci.* 825:240-257.
Doppenberg et al. (1999) *J. Neurotrauma* 16:123-133.
Eichelbronner et al. (1999) *Am. J. Physiol.* 277 (*Heart Circ. Physiol.* 46): H290-H298.
Grocott et al. (1998) *Stroke* 29:1650-1655.
Kavanagh et al. (2001) *Int. J. Radiation Oncology Bio. Phys.* 49:1133-1139.
Khandelwal et al. (1996) *Rad. Oncol. Invest.* 4:51-59.
Khandelwal et al. (1999) *Brit. J. Cancer* 79:814-820.
Kilgore et al. (1999) *Circulation* 100 (Supp. II):II-351 to II-356.
Kunert et al. (1996) *Am. J. Physiol.* 271 (*Heart Circ. Physiol.* 40): H602-H613.
Kunert et al. (1996) *Microvasc. Res.* 52:58-68 (1996).
Oja et al. (1999) Magnetic Resonance in Medicine 42:617-626.
Oja et al. (1999) *J. of Cerebral Blood Flow and Metabolism* 19:1289-1295.
Mackensen et al. (2000) *Brain Res.* 853:15-21.
Pagel et al. (1998) in *Oxygen Transport to Tissues* XX 653-661 (Hudetz and Bruley, eds.) 527-531.
Randad et al. (1991) *J. Med. Chem.* 34:752-757.
Rockwell and Kelley (1998) *Rad. Oncol. Invest.* 6:199-208.
Safo et al. (2001) *Protein Sci.* 10:951-957.
Sarraf-Yazdi et al. (1999) *Brain Res.* 826:172-180.
Steffen, R. (1998) in *Oxygen Transport to Tissues* XX 653-661 (Hudetz and Bruley, eds.).
Teicher et al. (1996) *Drug Dev. Res.* 38(1):1-11.
Teicher et al. (1998) Vivo, *Cancer Chemother. Pharmacol.* 42:24-30.
Van Zijl et al. (1998) *Nat. Med.* 4(2):159-167.
Wahr et al. (2001) *Anesth. Analg.* 92:615-620.
Watson et al. (1997) *Stroke* 28:1624-1630.
Wei, et al. (1993) *Am. J. Physiol.* 265 (*Heart Circ. Physiol.* 34) H1439-H1443.
Weiss et al. (1999) *J. Clin. Invest.* 103:739-746.
Woods et al. (1998) *J Cardiovasc. Pharmacol.* 31:359-363.
Al-Hallaq et al. (1998) Int. J. Radiation Oncol. Biol. Phys. 41(1):151-159.
Al-Hallaq et al. (2000) Int. J. Radiation Oncol. Biol. Phys. 47(2):481-488.
Grella et al. (2000) J. Med. Chem. 43:4726-4737.
Jordan et al. (2000) Int. J. Radiation Oncol. Biol. Phys. 48(2):565-570.
Kleinberg et al. (Aug. 1999) J. of Clin. Oncol. 17(8):2593-2603.
Mejia et al. (1996) Circulation 94(1):I-607.
Muruganandham et al. (1999) Int. J. Radiation Oncol. Biol. Phys. 43(2):413-421.
Ogawa et al. (1993) MRM 29:205-210.
Ogawa et al. (Dec. 1990) Proc. Natl. Acad. Sci. USA 87:9868-9872.
Ogawa et al. (Mar. 1993) Biophys. J. 64:803-812.
Prasad and Epstein (1999) Kidney International 55:294-298.

(Continued)

*Primary Examiner*—Michael Hartley
(74) *Attorney, Agent, or Firm*—Swanson & Bratschun, LLC

(57) ABSTRACT

Method for obtaining BOLD MRI images with allosteric effector compounds are disclosed. Methods for the determination of tumor oxygenation and for an optimal time for initiating radiation therapy are also disclosed.

11 Claims, 9 Drawing Sheets

(5 of 9 Drawing Sheet(s) Filed in Color)

OTHER PUBLICATIONS

Wacker et al. (1999) Mag. Res. Mat. In Physics, Biology and Medicine 8:48-54.
Winslow (2000) Current Opinion in Cardiovascular, Pulmonary and Renal Investigational Drugs 2(2):131-137.
Wireko et al. (1991) J. Med. Chem. 34:758-767.
Amorino et al. (2001) Rad. Res. 156:294-300.
Holmer (2001) Onco. Spectr 2(1):48-60.
Khandelwal et al. (1993) Am. J. Physiol. 265(Heart Circ. Physiol. 34):H1450-H1453.
Pagel et al. (1998) J. Pharmacol. Exp. Ther. 285:1-8.
Tomera (2000) Drugs of Today 36:355-367.

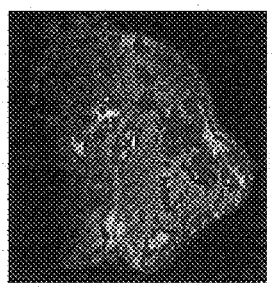
Fig. 5A
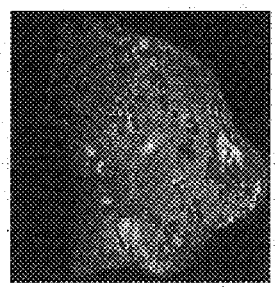
Fig. 5B
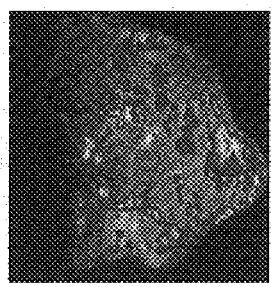
Fig. 5C
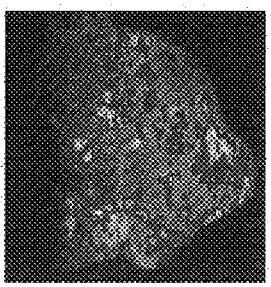
Fig. 5D
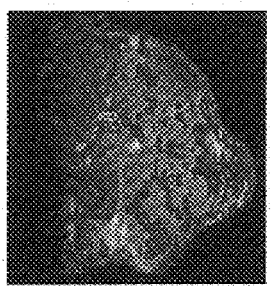
Fig. 5E
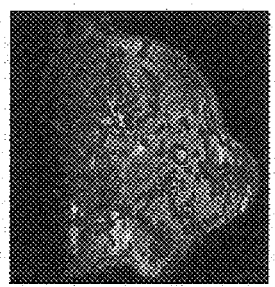
Fig. 5F
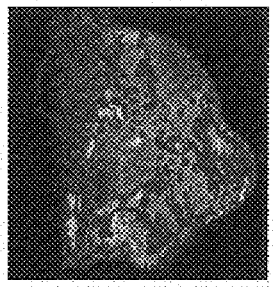
Fig. 5G

METHODS AND REAGENTS TO ACQUIRE MRI SIGNALS AND IMAGES

CROSS-REFERENCE TO RELATED APPLICATIONS

This application claims priority under 35 U.S.C. § 119 from U.S. Application Ser. No. 60/271,237, filed Feb. 23, 2001.

FIELD OF THE INVENTION

This invention relates generally to magnetic resonance imaging (MRI). More particularly, the present invention relates to applications for fMRI or BOLD MRI.

BACKGROUND OF THE INVENTION

Magnetic resonance imaging (MRI) is a versatile technique which is used to obtain functional and anatomical information with a high spatial (mm) resolution, such that most structural changes in the brain and other organs can be detected. MRI does have limitations. MRI does not show up such critical factors as receptor binding (important in drug studies) or functional features such as blood flow or electrical activity. It has no dynamic ability (except to image structural changes which, of course, occur over weeks or years). Finally, the MRI technique can induce tissue heating (from the RF field) as well as electrical currents in conductive tissues from the static and dynamic impressed magnetic fields (static fields induce currents due to blood flowing relative to the field).

Recently, it has been established that subtle physiological alterations, such as changes in blood flow, blood volume, and blood oxygenation can be detected using MRI. See Ogawa, et al., *Proc. Nat. Acad. Sci.* 87:9868–72 (1990); Ogawa, et al., *Biophys. J.* 64:803–12 (1993); Ogawa, et al., *Magn. Reson. Med.* 29:205–10 (1993). Ogawa, et al., showed that the MRI signal alterations from these changes were related in the changes in the concentration of deoxyhemoglobin. This functional MRI (fMRI) works by imaging blood oxygenation and is also called BOLD (Blood Oxygen Level Dependence). Van Zijl, et al., showed that hemoglobin acts as a natural intravascular contrast agent. BOLD relies on mechanisms which overcompensate for oxygen usage (activation causes an influx of oxygenated blood in excess of that used and therefore the local oxyhemoglobin concentration increases). For example, oxygen is carried to the brain in the hemoglobin molecules of red blood cells. Deoxygenated hemoglobin is paramagnetic and therefore has a short T2 relaxation time. When neurons fire, they consume oxygen and local oxygen levels decrease briefly and then actually increase above the resting level as nearby capillaries dilate to allow more oxygenated blood into the active area. As the ratio of oxygenated to deoxygenated hemoglobin increases, so to does the signal recorded by MRI. As a result, intensity of images increases with the increase of brain activation. Van Zijl, et al. *Nature Med.*, 4:159–67 (1998) showed that is its possible to predict the magnitude of spin-echo MRI signal intensity changes on brain activation. Oja, et al., *Magn. Res. Med.* 42:617–26 (1999), indicate that the effects of spin-echo changes in draining veins are a major contribution to the total BOLD signal changes measured in the activated brain areas, and that existing theories for the spin-echo BOLD effect based on diffusion through field gradients are incompatible with observed data.

The oxygen extraction ratio (OER) of a tissue is the ratio of oxygen consumption to oxygen delivery for that tissue. In practice, the ratio of deoxyhemoglobin to total hemoglobin is a linear function of OER. Measuring OER in situ would allow for direct assessment of tissue viability and activity in any organ. Oja, et al., *J. Cereb. Blood Flow Metab.* 19:1289–95 (1999), report that OER can be determined using BOLD MRI. Oja, et al., measured the BOLD signal of venous blood draining from the brain after visual stimulation, rather than direct measurement of brain OER. Under normoxic conditions, BOLD contrast reflects the status of the venous microvasculature of the brain. The difference between images with and without an activation stimulus can be used to obtain functional maps of the brain.

While the vast majority of literature on BOLD MRI revolves around the brain, a few studies have been done in other contexts. Changes in the oxidation of the renal medulla, for example, can be monitored with BOLD MRI, as reported by Prasad and Epstein, *Kidney Int.* 55:294–98. Muruganadham, et al., *Int. J. Radiat. Oncol. Biol. Phys.* 43:413–21 (1999) report that the differential radiation response of murine normal and tumor tissue induced by diltiazem, a calcium channel blocker, correlates with diltiazem-increased tumor blood flow and tumor oxygenation as measured by BOLD MRI. Wacker, et al., *MAGMA* 8:48–54 (1999) have studied changes in myocardial oxygenation with BOLD MRI. Specifically, T2* measurements were used to create T2* maps, which revealed expected ischemic areas of myocardium in six patients. Dipyridamole (DIP), was used to increase myocardial blood flow for comparison. Jordan, et al., *Int. J. Radiat. Oncol. Biol. Phys.* 48:565–70 (2000) describe the effects of nitric oxide donor isosorbide dinitrate on $pO_2$ and blood flow in a murine tumor model with carbogen (a mixture of pure oxygen and carbon dioxide) as a reference treatment. The quantities of oxygen delivered to liver tumors were measured with BOLD and other methods. While isosorbide dinitrate improves blood flow alone, carbogen improves blood flow and hemoglobin oxygenation, resulting in increased BOLD image intensity.

While BOLD has great potential as an imaging technique, it currently suffers from a number of disadvantages. The increase in intensity of images due to decrease of T2 image is small (usually less than 2%), and unfortunately, easily obscured by noise and different artifacts. Other potential problems include the possible measurement of blood oxygen changes caused by previous processing, as hemodynamic changes involved in a change of task may take 3 to 8 seconds. Useful imaging still requires task repetition and image averaging, which can be unpleasant for the patient due to the noisy and claustrophobia-provoking environment of the MRI. Vascular drainage extending some centimeters from the local capillary network can create artifacts due to heating of the brain, rather than changes in blood flow. High powered MRI machines can alleviate some of these problems by increasing the signal to noise ratio and magnifying differences in the spatial propagation characteristics of various sources of T2 signal such as blood velocity effects and large vascular artifacts remote from the site of activity. Accordingly, there remains a need for improved BOLD imaging agents.

RSR13 2-[4-(((3,5-dimethylanilino)carbonyl)methyl)phenoxy]-2-methylpropionic acid):

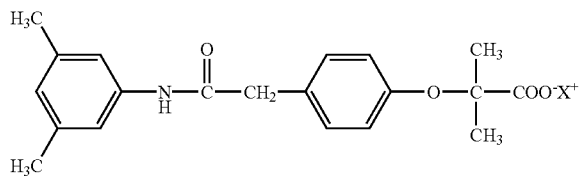

is an allosteric effector of hemoglobin, and has been shown to enhance tissue oxygenation in vivo. Sometimes, RSR13 is represented by the name 2-[4-[2-[(3,5-dimethylphenyl)amino]-2-oxoethyl]phenoxy]-2-methylpropanoic acid. In general RSR13 is administered as a physiologically acceptable salt, such as the monosodium salt; that is, $X^+$ is $Na^+$. RSR13 induces allosteric modification of hemoglobin, such that its binding affinity for oxygen is decreased, resulting in increased oxygen distribution to tissues by erythrocytes. RSR13 has been reported to enhance fractionated radiation therapy in mice bearing the Lewis lung carcinoma. See Teicher, (1996) *Drug Dev. Res.* 38:1–11. Enhancement of the effect of radiation was observed in EMT6 mouse mammary tumors by treatment of RSR13 plus oxygen breathing, with the absence of enhanced radiation effects in normal tissues. Rockwell and Kelley (1998) *Rad. Oncol. Invest.* 6:199–208. In addition, mouse fibrosarcoma tumor growth has been shown to be reduced by the combination of RSR13 and radiation relative to radiation alone. See Teicher, et al., ibid.; Khandelwal et al. (1996) *Rad. Oncol. Invest* 4:51–59.

Microelectrode measurements of $pO_2$ were used in the previous studies to monitor tumor oxygenation by RSR13. Although this method can provide an accurate determination of the oxygen levels in tumors, it is an invasive technique, and only measures the $pO_2$ levels near the electrode. Another technique used in these studies was the construction of hemoglobin (Hb)-$O_2$ dissociation curves from blood samples. Although this technique is less invasive, it requires multiple blood samples and does not specifically monitor tumor oxygenation, but measures whole body blood oxygen saturation.

SUMMARY OF THE INVENTION

The present invention is directed toward a method for measuring BOLD MRI signals and obtaining BOLD MRI images. The methods comprise administering an effective amount of an allosteric effector compound capable of decreasing hemoglobin binding affinity for oxygen, and performing a blood oxygen level-dependent magnetic resonance imaging scan.

The invention also provides a method of increasing the sensitivity of cells to the cytotoxic effects of ionizing radiation comprising contacting the cells with an amount of a compound effective to oxygenate the cells, measuring the oxygenation of the cells, and administering an effective cytotoxic dose of ionizing radiation to the cells.

Also within the scope of the present invention is a method of measuring tumor oxygenation, comprising administering an effective amount of an allosteric effector compound capable of decreasing hemoglobin binding affinity for oxygen, and performing a blood oxygen level-dependent magnetic resonance imaging scan. Also within the scope of the present invention is a method for determining an optimal time for the initiation of radiation therapy, comprising administering an effective amount of an allosteric effector compound capable of decreasing hemoglobin binding affinity for oxygen, measuring the blood oxygen level dependent signal ratio, and determining the time required for a maximum increase in the blood oxygen level dependent signal ratio.

The invention further provides a method of diagnosing an abnormal pathology, comprising introducing an allosteric effector compound into a patient suspected of having the abnormal pathology, performing a blood oxygen level-dependent magnetic resonance imaging scan of the patient, and detecting an increase in blood oxygen level-dependent magnetic resonance imaging signal.

The invention further provides a method of imaging glioblastoma multiforme, comprising administering an effective amount of an allosteric effector compound capable of decreasing hemoglobin binding affinity for oxygen, and performing a blood oxygen level-dependent magnetic resonance imaging scan.

The allosteric effector compounds useful in the invention are, a compound having the formula:

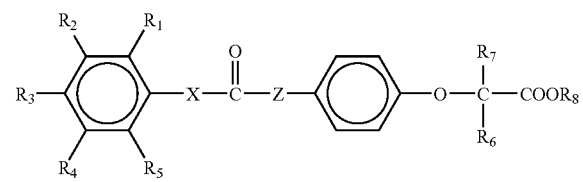

where $R_{1-5}$ may be hydrogen, halogen, or a substituted or unsubstituted $C_{1-3}$ alkyl group and may be the same or different, $R_{6-7}$ may each be hydrogen or methyl and may be the same or different, and $R_8$ may be hydrogen, a substituted or unsubstituted $C_{1-3}$ alkyl group, or a salt cation, and X and Z are $CH_2$, NH, or O;

a compound having the formula:

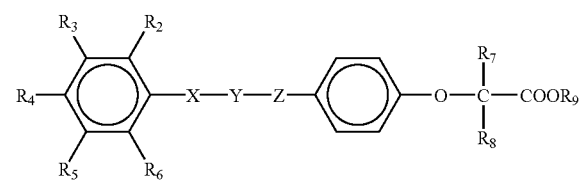

where X and Z may each be $CH_2$, CO, NH or O, and Y may be CO or NH, which the caveat that X, Y, and Z must all be different from each other, and $R_{2-6}$ can be the hydrogen, halogen, substituted or unsubstituted $C_{1-3}$ alkyl groups, and may be the same or different, $R_{7-8}$ can be hydrogens, methyls, ethyls, or alkyl groups in a ring connecting the two, and $R_9$ can be a hydrogen, lower alkyl, or salt cation;

a compound having the formula:

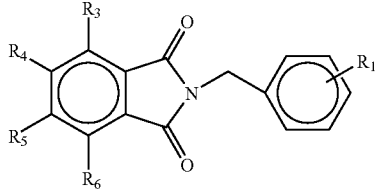

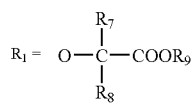

where $R_{3-6}$ can be the hydrogen, halogen, substituted or unsubstituted $C_{1-3}$ alkyl group, or a $C_{1-3}$ ether or ester, and these moieties may be the same or different, or alkyl moieties of an aromatic or aliphatic ring incorporating two of the $R_{3-6}$, $R_1$ can be connected to any position on the phenyl ring, and sites $R_{7-8}$ can be hydrogen, halogen, methyl, ethyl, and these moieties may be the same or different, or alkyl groups in a ring connecting the two, and $R_9$ can be a hydrogen, halogen, $C_{1-3}$ lower alkyl, or salt cation;

a compound having the formula:

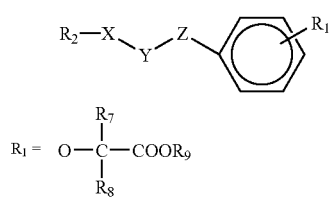

where $R_1$ can be connected to any position on the phenyl ring, and sites $R_{7-8}$ can be hydrogen, halogen, methyl, ethyl, and these moieties may be the same or different, or alkyl groups in a ring connecting the two, and $R_2$ is defined as a substituted or unsubstituted aromatic compound, a substituted or unsubstituted alkyl ring compound, or a substituted or unsubstituted phthalimide compound, X is a carboxyl, Y is a nitrogen, and $R_2$ completes the phthalimide compound by being bonded to both X and Y; and where X, Y, and Z, may either be $CH_2$, NH, O, or N, with the caveat that each are different from the other;

a compound having the formula:

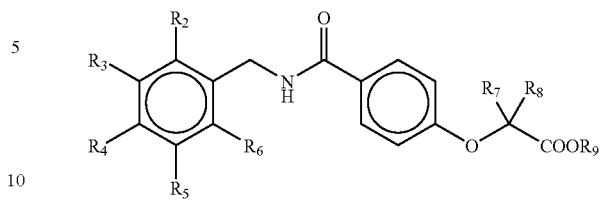

where $R_2$, $R_3$, $R_4$, $R_5$, and $R_6$ may be hydrogen, halogen, or alkyl groups and may be the same or different, $R_7$ and $R_8$ may be hydrogen or methyl groups and may be the same or different, and where the $R_9$ moiety is hydrogen or a salt cation;

a compound having the formula:

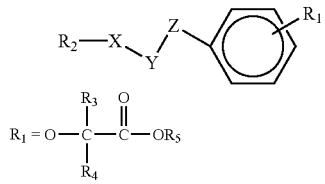

where $R_2$ is a substituted or unsubstituted aromatic compound, or a substituted or unsubstituted alkyl ring compound, or a substituted or unsubstituted phthalimide compound that incorporates X and Y, X is a carbonyl, Y is a nitrogen, and $R_2$ completes the phthalimide compound by being bonded to both X and Y, and where X, Y, and Z are $CH_2$, NH, S, $SO_2$, CO, O or N with the caveat that X, Y, and Z are each different from one another, and where $R_1$ can be connected to any position on the phenyl ring, and $R_3$ and $R_4$ are hydrogen, halogen, methyl, ethyl, propyl, isopropyl, neopentyl, butyl, or substituted or unsubstituted aryl groups and these moieties may be the same or different, or alkyl moieties as part of an aliphatic ring connecting $R_3$ and $R_4$, and $R_5$ is a hydrogen, halogen, $C_{1-3}$ lower alkyl, or a salt cation;

a compound having the formula:

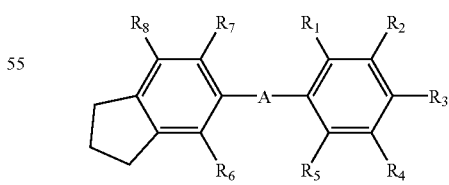

where A is a chemical bridge which includes two to four chemical moieties bonded together, the chemical moieties in A are selected from the group consisting of CO, O, S, $SO_2$, NH, $NR_9$ where $R_9$ is a $C_{1-6}$ alkyl group, $CH_2$, CH, and C, with the proviso that, except in the case where A contains two identical CH and C moieties positioned adjacent one another to form an alkene or alkyne, the chemical moieties in A are each different from one another, and at least one of $R_{1-5}$ is substituted with a compound having the chemical formula:

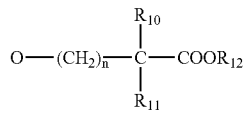

where n is zero to five, where $R_{10}$ and $R_{11}$ are selected from the group consisting of hydrogen, halogen, $C_{1-12}$ alkyl groups, carboxylic acids and esters, aromatic or heteroatomic groups, and these moieties may be the same or different, or alkyl moieties of part of an aliphatic ring connecting $R_{10}$ and $R_{11}$, and where $R_{12}$ is a hydrogen, halogen, salt cation, metal, or $C_{1-6}$ alkyl group, and wherein a remainder of the $R_{1-5}$ moieties and the $R_{6-8}$ moieties are selected from the group consisting of hydrogen, halogen, $C_{1-6}$ alkyl groups, $C_{1-6}$ ether or esters, aromatics and heteroaromatics, and alkyl moieties of an aliphatic ring connecting two sites on a phenyl group;

a compound having the formula:

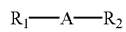

where $R_1$ and $R_2$ each are a substituted or unsubstituted aromatic or heteroaromatic compounds, or a substituted or unsubstituted alkyl or heteroalkyl ring compound, or a substituted or unsubstituted phthalimide compound, and where $R_1$ and $R_2$ may be the same or different, where A is a chemical bridge which includes three chemical moieties bonded together between $R_1$ and $R_2$, wherein the chemical moieties in A are selected from the group consisting of CO, O, S, SO$_2$, NH, NR$_3$ where $R_3$ is $C_{1-6}$ alkyl group, NR$_4$ where $R_4$ includes two carbonyls as part of a phthalimide compound formed with $R_1$ or $R_2$, CH$_2$, CH, and C, and where at least one of $R_1$ and $R_2$ is substituted with a compounds having the chemical formula:

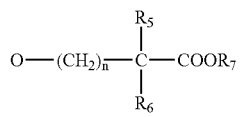

where n is zero to five, where $R_5$ and $R_6$ are selected from the group consisting of hydrogen, halogen, substituted or unsubstituted $C_{1-12}$ alkyl groups, carboxylic acid and ester groups, substituted or unsubstituted aromatic or heteroaromatic groups, and these moieties may be the same or different, or alkyl moieties of part of an aliphatic ring connecting $R_5$ and $R_6$, and where $R_7$ is a hydrogen, halogen, salt cation, metal, or substituted or unsubstituted $C_{1-6}$ alkyl group;

a compound having the formula:

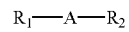

where $R_1$ and $R_2$ each are a substituted or unsubstituted aromatic or heteroaromatic compound, or substituted or unsubstituted alkyl or heteroalkyl ring compound, or a substituted or unsubstituted phthalimide compound, and where $R_1$ and $R_2$ may be the same or different, where A is a chemical bridge which includes two to four chemical moieties bonded together between $R_1$ and $R_2$, wherein at least one of $R_1$ or $R_2$ is substituted with a compound having the chemical formula:

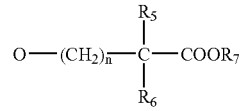

where n is zero to five, where $R_5$ and $R_6$ are selected from the group consisting of hydrogen, halogen, substituted or unsubstituted $C_{1-12}$ alkyl groups, carboxylic acid and ester, substituted or unsubstituted aromatic or heteroaromatic groups, and these moieties may be the same or different, or alkyl moieties of part of an aliphatic ring connecting $R_5$ and $R_6$, and where $R_7$ is a hydrogen, halogen, salt cation, metal, or substituted or unsubstituted $C_{1-6}$ alkyl group; and/or a compound having the formula:

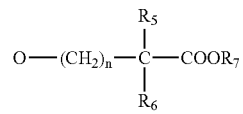

where $R_1$ is selected from the group consisting of optionally substituted phenyl, adamantyl, napthyl, and indanyl, $R_{2-3}$ are alkyl moieties of a $C_{3-6}$ alkyl ring connecting $R_2$ and $R_3$, and $R_4$ is a hydrogen, a monovalent salt cation, or a $C_{1-3}$ lower alkyl.

BRIEF DESCRIPTION OF THE FIGURES

This patent or application file contains at least one drawing executed in color. Copies of this patent or patent application publication with color drawing(s) will be provided by the Office upon request and payment of the necessary fee.

FIG. 2A is an image from a control, saline-treated mouse, and

FIG. 2B is an image from a mouse treated with RSR13.

FIGS. 5A–G show color maps of percent T2* dependent gradient echo signal increase from baseline post-injection of 100 mg/kg RSR13 at times 0 (FIG. 5A), 10 (FIG. 5B), 20 (FIG. 5C), 30 (FIG. 5D), 40 (FIG. 5E), 50 (FIG. 5F) and 60 (FIG. 5G) minutes. Color maps are superimposed over spin echo images of a single slice through the tumor.

FIGS. 6A–G shows color maps of percent T2* dependent gradient echo signal increase from baseline post-injection of 200 mg/kg RSR13 at times 0 (FIG. 7A), 10 (FIG. 7B), 20 (FIG. 7C), 30 (FIG. 7D), 40 (FIG. 7E), 50 (FIG. 7F) and 60 (FIG. 7G) minutes. Color maps are superimposed over spin echo images of a single slice through the tumor.

DETAILED DESCRIPTION OF THE INVENTION

Figure 1:
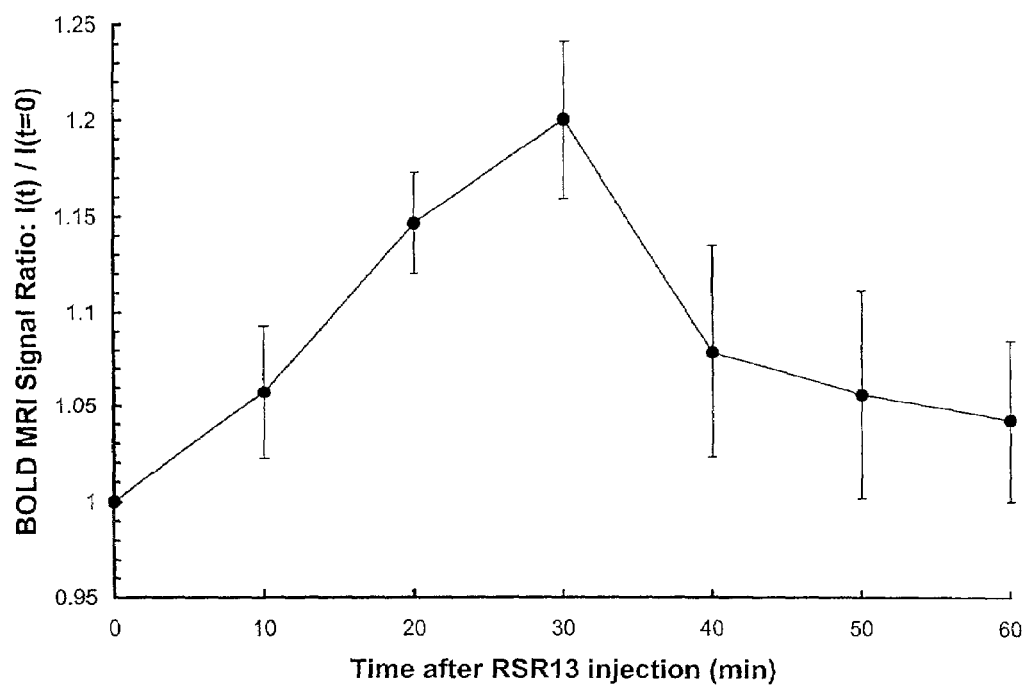
FIG. 1 shows time dependence of RSR13-induced changes in tumor oxygenation. Nude mice with human lung carcinoma xenografts in the flank region were injected i.p. with 200 mg/kg RSR13 at t=0 min, and MR images were acquired immediately and at 10 min intervals. Eight independent experiments were performed (1 mouse/exp), and error bars represent±SEM values (n=8).

The use of the allosteric effector compounds in the present invention can result in valuable utility for a variety of applications. Because the allosteric effector compounds used in the present invention are capable of allosterically modifying the oxygenation of hemoglobin, they are able to alter the ratio of oxy- to deoxy-hemoglobin, thus allowing for a stronger BOLD MRI signal. In this sense, the allosteric effector compounds are useful simply to obtain a BOLD MRI signal and make for more accurate quantitation of biological events or physiology due to the improved signal to noise signal.

In another embodiment of the present invention, the use of allosteric effector compounds are useful to observe dynamic characteristics within the tissue being evaluated by BOLD MRI. Because the allosteric effect of the allosteric effector compounds follows a defined time course, it is possible to detect dynamic changes in the tissue under study because the oxy-/deoxy-hemoglobin ratio will be changing—at first increasing to a minimum value, and then returning to its original levels within a tissue.

Also the use of BOLD MRI in conjunction with therapeutic applications of the hemoglobin allosteric effectors of the present invention is included within the present invention. For example, in some protocols RSR13 is administered in conjunction with chemotherapeutic agents or radiation that are enhanced by the oxygenation of tissue afforded by the administration of RSR13. In order to maximize the effectiveness of such protocols, the use of BOLD MRI enables a dynamic evaluation of when the tissue oxygenation is maximized, thereby allowing for optimization of the chemotherapeutic treatment.

BOLD MRI Measurement

The present invention is directed toward allosteric effector compounds useful in BOLD MRI methods. Allosteric effector compounds useful in the present invention fall into several categories:

Group I: 2-[4-((aryl)acetamido)phenoxy]2-methyl propionic acid compounds having the general structural formula:

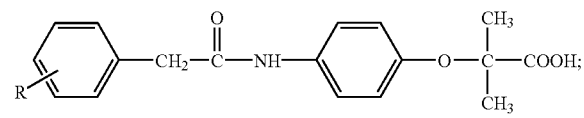

group II: 2-[4-(((aryl)oxy)carbonyl)amino) phenoxy]-2-methyl propionic acid compounds having the general structural formula

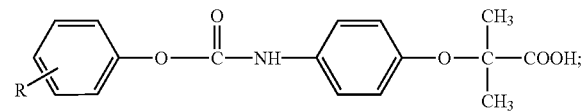

group III: 2-[4 ((((aryl)amino)carbonyl) methyl)phenoxy]-2-methyl propionic acid compounds having the general structural formulae

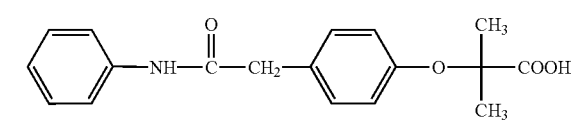

and

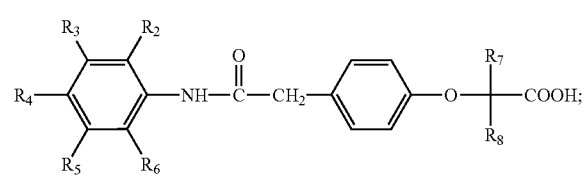

group IV: 2-[4-(((aryl)amino)carbonyl) oxy)phenoxy]-2-methyl propionic acid compounds having the general structural formula

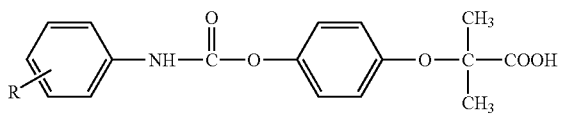

In one subset of compounds defined by the formula

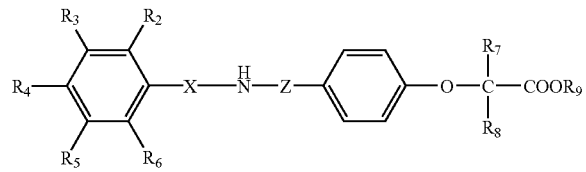

X and Z may each be CO or $CH_2$, with the caveat that when X is CO, Z is $CH_2$, and when X is $CH_2$, Z is CO. This subset of compounds may be conveniently divided into two additional groupings as follows:

Group V: 2-[4-(((aryloyl)amino)methyl)phenoxy]-2-methyl propionic acid compounds having the general structural formula

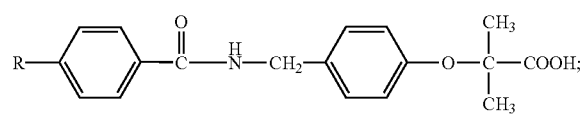

Group VI: 2-[4-((((aryl)methyl)amino) carbonyl)phenoxy]-2-methyl propionic acid compounds having the general structural formula; and

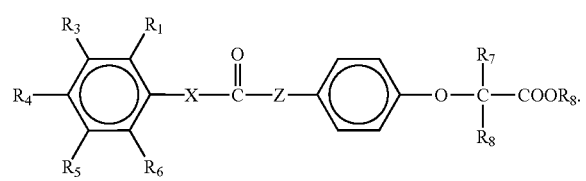

Group VII has the general structural formula:

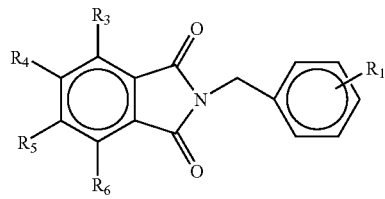

The image enhancing agents of the present invention are capable of allosterically effecting hemoglobin to cause a change in the oxy-/deoxy- hemoglobin ratio. Allosteric effector compounds useful in the present invention include compounds disclosed in U.S. Pat. No. 5,049,695, including

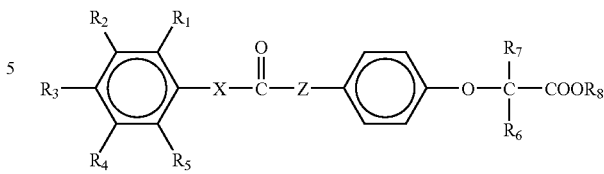

where $R_{1-5}$ may be hydrogen, halogen, or a substituted or unsubstituted $C_{1-3}$ alkyl group and may be the same or different, wherein $R_{6-7}$ may each be hydrogen or methyl and may be the same or different, and wherein $R_8$ may be hydrogen, a substituted or unsubstituted $C_{1-3}$ alkyl group, or a salt cation, and where X and Z are $CH_2$, NH, or O. Other allosteric effector compounds useful in the present invention disclosed in U.S. Pat. No. 5,122,539 include

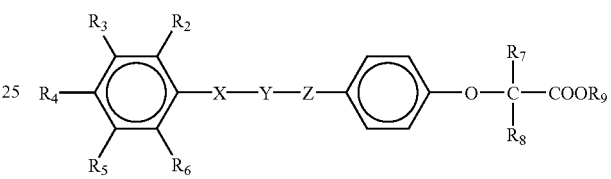

where X and Z may each be $CH_2$, CO, NH or O, and Y may be CO or NH, which the caveat that X, Y, and Z must all be different from each other. $R_{2-6}$ can be the hydrogen, halogen, substituted or unsubstituted $C_{1-3}$ alkyl groups, and may be the same or different, $R_{7-8}$ can be hydrogens, methyls, ethyls, or alkyl groups in a ring connecting the two, and $R_9$ can be a hydrogen, lower alkyl, or salt cation.

Also included as allosteric effector compounds useful in the present invention are compounds disclosed in U.S. Pat. Nos. 5,248,785 and 5,250,701, including

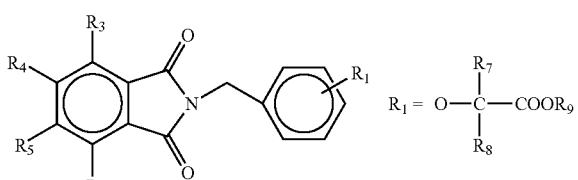

where $R_{3-6}$ can be the hydrogen, halogen, substituted or unsubstituted $C_{1-3}$ alkyl group, or a $C_{1-3}$ ether or ester, and these moieties may be the same or different, or alkyl moieties of an aromatic or aliphatic ring incorporating two of the $R_{3-6}$, and where $R_1$ can be connected to any position on the phenyl ring, and sites $R_{7-8}$ can be hydrogen, halogen, methyl, ethyl, and these moieties may be the same or different, or alkyl groups in a ring connecting the two, and $R_9$ can be a hydrogen, halogen, $C_{1-3}$ lower alkyl, or salt cation.

Also included as allosteric effector compounds useful in the present invention are compounds disclosed in U.S. Pat. No. 5,290,803 including

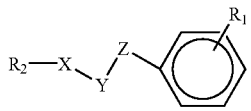

where $R_1$ is a tail structure as defined above in connection with U.S. Pat. No. 5,248,785, and $R_2$ is defined as a substituted or unsubstituted aromatic compound, a substituted or unsubstituted alkyl ring compound, or a substituted or unsubstituted phthalimide compound X is a carboxyl, Y is a nitrogen and $R_2$ completes the phthalimide compound by being bonded to both X and Y; and where X, Y, and Z, may either be $CH_2$, NH, O, or N, with the caveat that each are different from the other.

Also included as allosteric effector compounds useful in the present invention are compounds disclosed in U.S. Pat. No. 5,382,680 including

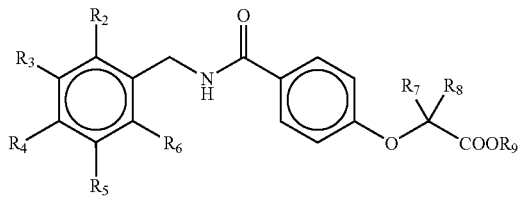

wherein the $R_2$, $R_3$, $R_4$, $R_5$, and $R_6$ moieties may be hydrogen, halogen, or alkyl groups and may be the same or different, wherein the $R_7$ and $R_8$ moieties may be hydrogen or methyl groups and may be the same or different, and wherein the $R_9$ moiety is hydrogen or a salt cation.

Also included as allosteric effector compounds useful in the present invention are compounds disclosed in U.S. Pat. No. 5,432,191 including

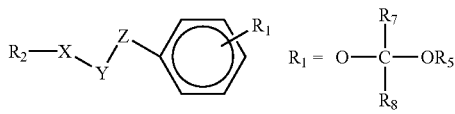

where $R_2$ is a substituted or unsubstituted aromatic compound, or a substituted or unsubstituted alkyl ring compound, or a substituted or unsubstituted phthalimide compound that incorporates X and Y where X is a carbonyl, Y is a nitrogen and $R_2$ completes the phthalimide compound by being bonded to both X and Y, and where X, Y, and Z are $CH_2$, NH, S, $SO_2$, CO, O or N with the caveat that the X, Y, and Z moieties are each different from one another, and where $R_1$ can be connected to any position on the phenyl ring, and $R_3$ and $R_4$ are hydrogen, halogen, methyl, ethyl, propyl, isopropyl, neopentyl, butyl, or substituted or unsubstituted aryl groups and these moieties may be the same or different, or alkyl moieties as part of an aliphatic ring connecting $R_3$ and $R_4$, and $R_5$ is a hydrogen, halogen, $C_{1-3}$ lower alkyl, or a salt cation.

Also included as allosteric effector compounds useful in the present invention are compounds disclosed in U.S. Pat. No. 5,591,892 including

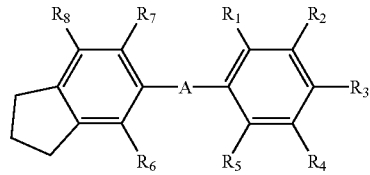

where A is a chemical bridge which includes two to four chemical moieties bonded together, wherein the chemical moieties in A are selected from the group consisting of CO, O, S, $SO_2$, NH, $NR_9$ where $R_9$ is a $C_{1-6}$ alkyl group, $CH_2$, CH, and C, with the proviso that, except in the case where A contains two identical CH and C moieties positioned adjacent one another to form an alkene or alkyne, the chemical moieties in A are each different from one another, and wherein at least one of $R_{1-5}$ is substituted with a compound having the chemical formula:

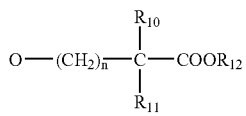

where n is zero to five, where $R_{10}$ and $R_{11}$ are selected from the group consisting of hydrogen, halogen, $C_{1-12}$ alkyl groups, carboxylic acids and esters, aromatic or heteroatomic groups, and these moieties may be the same or different, or alkyl moieties of part of an aliphatic ring connecting $R_{10}$ and $R_{11}$, and where $R_{12}$ is a hydrogen, halogen, salt cation, metal, or $C_{1-6}$ alkyl group, and wherein a remainder of the $R_{1-5}$ moieties and the $R_{6-8}$ moieties are selected from the group consisting of hydrogen, halogen, $C_{1-6}$ alkyl groups, $C_{1-6}$ ether or esters, aromatics and heteroaromatics, and alkyl moieties of an aliphatic ring connecting two sites on a phenyl group.

Also included as allosteric effector compounds useful in the present invention are compounds disclosed in U.S. Pat. No. 5,648,375 including a compound of the formula $R_1$-A-$R_2$ where $R_1$ and $R_2$ each are a substituted or unsubstituted aromatic or heteroaromatic compounds, or a substituted or unsubstituted alkyl or heteroalkyl ring compound, or a substituted or unsubstituted phthalimide compound, and where $R_1$ and $R_2$ may be the same or different, where A is a chemical bridge which includes 3 chemical moieties bonded together between $R_1$ and $R_2$, wherein the chemical moieties in A are selected from the group consisting of CO, O, S, $SO_2$, NH, $NR_3$ where $R_3$ is $C_{1-6}$ alkyl group, $NR_4$ where $R_4$ includes two carbonyls as part of a phthalimide compound formed with $R_1$ or $R_2$, $CH_2$, CH, and C, and where at least one of $R_1$ and $R_2$ is substituted with a compounds having the chemical formula:

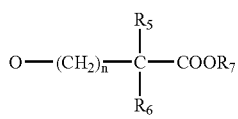

where n is zero to five, where $R_5$ and $R_6$ are selected from the group consisting of hydrogen, halogen, substituted or unsubstituted $C_{1-12}$ alkyl groups, carboxylic acid and ester groups, substituted or unsubstituted aromatic or heteroaromatic groups, and these moieties may be the same or different, or alkyl moieties of part of an aliphatic ring connecting $R_5$ and $R_6$, and where $R_7$ is a hydrogen, halogen, salt cation, metal, or substituted or unsubstituted $C_{1-6}$ alkyl group.

Also included as allosteric effector compounds useful in the present invention are compounds disclosed in U.S. Pat. No. 5,661,182, including an allosteric effector molecule which (i) binds to only one pair of symmetry related sites in the central water cavity of hemoglobin at the Lys 99 α, Arg 141 α, and Asn 108 β residues, each pair of symmetry related sites having residues on three separate sub-units of the hemoglobin, (ii) stabilizes the hemoglobin in a lower oxygen affinity state, and (iii) is active in the presence of normal concentrations of serum albumin in the blood, the allosteric effector molecule (a) maintains greater than sixty percent of its activity in terms of right shifting the oxygen dissociation curve of hemoglobin for a buffered red cell suspension at pH 7.4, in 140 mM NaCl and 50 mM bis-Tris buffer at 37° C., which contains 20–25 μM hemoglobin on a tetramer basis, 50 M serum albumin, and 0.5 mM of the allosteric effector molecule, relative to the buffered red cell suspension without 50 μM serum albumin, and (b) maintains greater than eighty percent of its activity in terms of a calculated oxygen delivery index for the buffered red cell suspension containing 50 μM serum albumin relative to the buffered red cell suspension without 50 μM serum albumin; and permitting the allosteric effector molecule to penetrate into erythrocytes in the blood and bind to the hemoglobin therein.

Also included as allosteric effector compounds useful in the present invention are compounds disclosed in U.S. Pat. Nos. 5,677,330, 5,705,521 and 5,927,283 including a compound of the formula $R_1$-A-$R_2$ where $R_1$ and $R_2$ each are a substituted or unsubstituted aromatic or heteroaromatic compound, or substituted or unsubstituted alkyl or heteroalkyl ring compound, or a substituted or unsubstituted phthalimide compound, and where $R_1$ and $R_2$ may be the same or different, where A is a chemical bridge which includes two to four chemical moieties bonded together between $R_1$ and $R_2$, wherein said chemical moieties in A are selected from the group consisting of CO, O, S, $SO_2$, NH, $NR_3$ where $R_3$ is a $C_{1-6}$ alkyl group, $NR_4$ where $R_4$ includes two carbonyls as part of a phthalimide compound formed with $R_1$ or $R_2$, $CH_2$, CH, and C, with the caveat that, except in the case where A contains two identical CH and C moieties positioned adjacent one another to form an alkene or alkyne, the chemical moieties in A are each different from one another, and wherein at least one of $R_1$ or $R_2$ is substituted with a compound having the chemical formula:

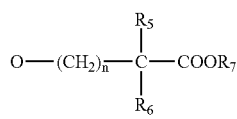

where n is zero to five, where $R_5$ and $R_6$ are selected from the group consisting of hydrogen, halogen, substituted or unsubstituted $C_{1-12}$ alkyl groups, carboxylic acid and ester, substituted or unsubstituted aromatic or heteroaromatic groups, and these moieties may be the same or different, or alkyl moieties of part of an aliphatic ring connecting $R_5$ and $R_6$, and where $R_7$ is a hydrogen, halogen, salt cation, metal, or substituted or unsubstituted $C_{1-6}$ alkyl group.

Also included as allosteric effector compounds useful in the present invention are compounds disclosed in U.S. Pat. No. 5,731,454 including

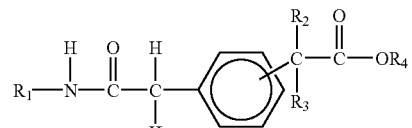

where $R_1$ is selected from the group consisting of optionally substituted phenyl, adamantyl, napthyl, and indanyl, $R_{2-3}$ are alkyl moieties of a $C_{3-6}$ alkyl ring connecting $R_2$ and $R_3$, and $R_4$ is a hydrogen, a monovalent salt cation, or a $C_{1-3}$ lower alkyl. Each of the above named patents, and all other patents and publications referred to herein, are incorporated by reference herein in their entirety.

In a preferred embodiment, the enhancement agent is RSR13 2-[4-(((3,5-dimethylanilino)carbonyl)methyl)phenoxy]-2-methylpropionic acid:

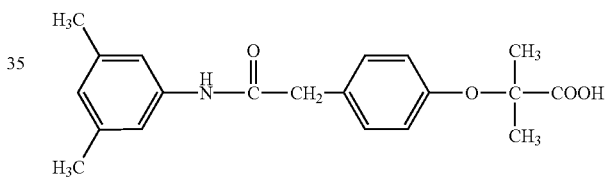

The compounds useful in the present invention, including RSR13, may be administered in the acid form, or in the form of a physiologically acceptable salt. The physiologically acceptable salt of RSR13 is represented as follows, where $X^+$ represents the cation of the physiologically acceptable salt:

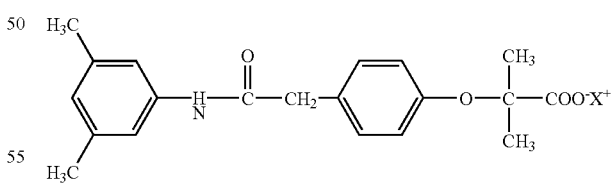

The salt may include compounds with inorganic or organic cationic counterions. For example, inorganic salts may include sodium, potassium, calcium, magnesium, zinc, or combinations thereof. Organic salts may include, for example, substituted or unsubstituted alkyl $C_1$–$C_6$ compounds or other common organic counterions.

In a particularly preferred embodiment, the physiologically acceptable salt is the sodium salt ($C_{20}H_{22}NO_4Na$; Molecular Weight=363.38):

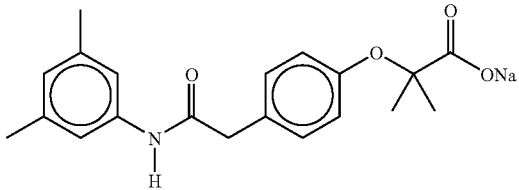

RSR13 shifts the hemoglobin oxygen dissociation curve to the right. It stabilizes the deoxyhemoglobin state (increasing deoxyhemoglobin concentration), resulting in increased oxygen release in tissues at a given oxygen tension in the capillary. The additional oxygen released may be available to diffuse to hypoxic areas of tumor or brain. There is substantial evidence from animal models and limited data in human patients that tumor oxygenation can be substantially increased by RSR13.

It has been shown by Ogawa and Lee, as well as others, that the equation for the relationship between the BOLD MRI signal ratio (which they have denoted S/So) and blood oxygenation (Y) is:

$$\ln(S/S_0) = mY + b,$$

where m=the slope and b=intercept. Thus, the increases observed in the BOLD MRI signal ratio (which is denoted herein as $I/I_0$) are linearly related with increases in blood oxygenation. Since tumors require vascularization for growth, and the signal changes were observed within the tumor boundaries, the signal ratio is correlated with tumor oxygenation.

Disclosed herein is a method to specifically monitor tumor oxygenation by RSR13 which is non-invasive and can provide spatial quantification of oxygenation in tumor slices. In particular, the method comprises administering a allosteric effector compound to a patient and measuring BOLD MRI signal of the patient. The present invention is also directed toward methods for enhancing BOLD MRI images. The method, in its most general form comprises administering to a patient an image enhancing agent of the present invention, and scanning the patient using BOLD MRI. This invention also provides a method of diagnosing abnormal pathology in vivo comprising introducing an image enhancing agent into a patient suspected of having the abnormal pathology, and scanning the patient using BOLD MRI.

Experiments were performed to show the dose response for RSR13-induced MRI signal increases. Mice with human lung carcinoma xenografts were used. The methods used were based upon the established observation that the MRI signal ratio varies linearly with the oxygen saturation of human blood (% Hb-$O_2$).

Preliminary experiments were performed to determine the dose response for RSR13-induced increases in MRI signal. Four experiments (1 mouse/experiment) were performed, using 0 mg/kg, 100 mg/kg, 200 mg/kg, and 300 mg/kg RSR13. Images of the tumors were acquired at 10 minute intervals, and the signal Intensity (t=30 min)/Intensity (t=0) was calculated. The results of these dose dependence experiments, at t=30 min, are shown in Table 1. A time of 30 min was chosen for this analysis, since this is the approximate time previously reported to yield the maximum tissue oxygenation with RSR13. The signal ratio increased in a dose-dependent fashion and reached a plateau at 200 mg/kg. Since this dose was in reasonable agreement with the optimum RSR13 dose reported by others, a 200 mg/kg dose was chosen for further studies.

TABLE 1

Preliminary experiments testing dose response of BOLD image signal ratio 30 minutes after injection of RSR13.

| Mouse # | RSR13 dose (mg/kg) | Change in BOLD MRI signal: (Intensity (t = 30 min)/Intensity (t = 0)) |
|---|---|---|
| Mouse A | 0 | 1.03 |
| Mouse B | 100 | 1.13 |
| Mouse C | 200 | 1.20 |
| Mouse D | 300 | 1.19 |

Figure 2A:
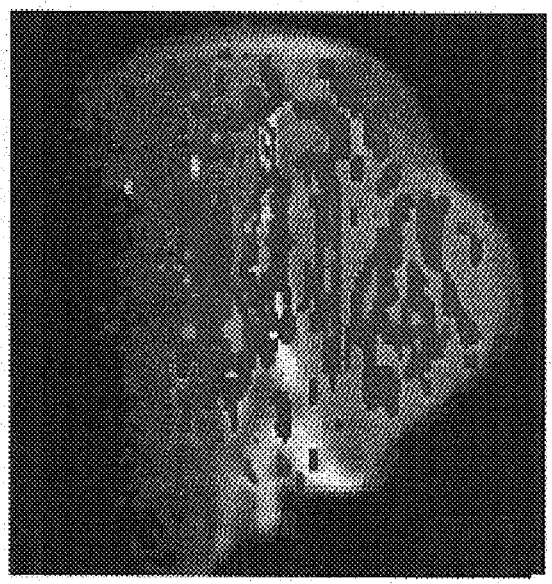
FIG. 2A and FIG. 2B show color images of percent T2* dependent gradient echo signal increase from baseline at 30 min post-injection, representative of those used to calculate the ratios shown in FIG. 1. The color scale represents the ratio: Intensity (t=30 min)/Intensity (t=0). Color maps are superimposed over spin echo images of a single slice through the tumor.
Figure 2A:
Figure 2B:
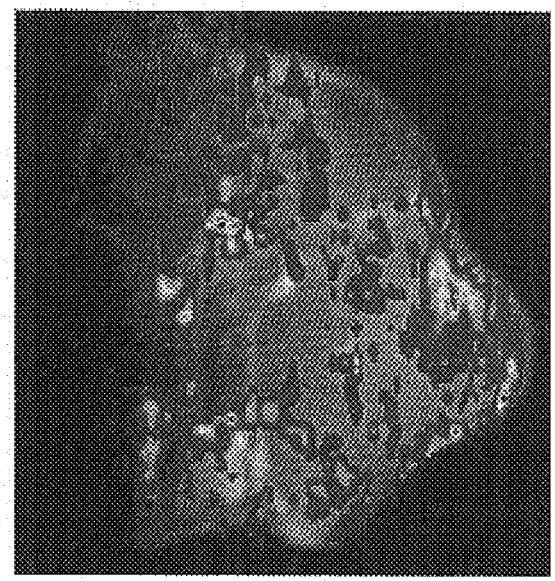

The time dependence of BOLD MRI signal using a single RSR13 dose (200 mg/kg) is shown in FIG. 1. Eight experiments were performed (1 mouse/exp), and the mean and SEM values for the signal ratio were calculated. The MRI signal ratio reached a maximum at 30 min after RSR13 injection (FIGS. 7A–G). There was a statistically significant change between t=10 and 20 min (increasing 9%, P=0.05). A statistically significant change was observed between t=10 and 30 min (increasing 14%, P=0.04). The changes between t=10 and 40, 50, or 60 min were not statistically significant (P≧0.05). FIG. 2 shows representative images which were used to calculate the ratios given in FIG. 1 and Table 1. The color scale represents the ratio: Intensity (t=30 min)/Intensity (t=0).

The imaging agents of the present invention are useful in imaging a patient generally, and/or in specifically diagnosing the presence of diseased tissue in a patient. The imaging process may be carried out by administering an imaging agent of the invention to a patient, and then scanning the patient using BOLD MRI to obtain visible images of an internal region of a patient and/or of any diseased tissue in that region. By region of a patient, it is meant the whole patient, or a particular area or portion of the patient. The imaging agents may be employed to provide images of the brain, vasculature, heart, liver, and spleen, and in imaging the gastrointestinal region or other body cavities.

The imaging agents of the present invention are also useful in conjunction with chemotherapeutic agents. In one embodiment, the invention provides a method of imaging glioblastoma multiforme, comprising administering an effective amount of an allosteric effector compound and performing a BOLD MRI scan. An exemplary method is provided in Example 5. Other methods which may be used in conjunction with a BOLD MRI scan include those disclosed in Kleinberg, et al., J. Clin. Oncol. (1999) 17:2393–2603. In another embodiment, the imaging agents of the present invention may be administered with standard chemotherapeutic agents. In the case of imaging glioblastoma mutiforme, the imaging agent can be administered along with BCNU (Carmustine), for example.

In some embodiments, RSR13 is administered intravenously at a concentration of 20 mg/mL via a central venous access device administered over 30 minutes. In other embodiments, it is given as a single administration at 10 mg/mL via a peripheral vein administered over 90.

In some embodiments, RSR13 at 25–200 mg/kg is administered over 30 minutes as daily intravenous doses by central venous access device with concurrent supplemental oxygen administration. RSR13 is administered every day of a fractionated course of radiation therapy. Radiation therapy is preferably administered within 30 minutes of end-infusion.

For BCNU chemotherapy studies, RSR13 at about 25–200 mg/kg is preferably administered in the same manner but followed by BCNU within 30 minutes of end-infusion. RSR13/BCNU is preferably administered once every 6 weeks for a total of 6 cycles. In other embodiments, RSR13 is administered at 50–150 mg/kg. In further embodiments, RSR13 is administered at 75–125 mg/kg. In still further embodiments, RSR13 is administered at 85–110 mg/kg.

Radiosensitization

The present invention provides a means to radiosensitize a tumor in a subject, such that the tumor is more susceptible to the effects of radiation, including tumor cell killing. For convenience, reference is made generally herein to tumor cell "killing." It should be recognized, however, that an increased susceptibility of a tumor cell to any of the effects of radiation can provide a significant therapeutic advantage to a cancer patient.

In a preferred embodiment, the radiosensitizing agent is RSR13 [2,4-(((3,5-dimethylanilino)carbonyl)methyl)phenoxy]-2-methylpropionic acid or a physiologically acceptable salt thereof, preferably the sodium salt.

This invention provides a method of increasing the sensitivity of cells to the cytotoxic effects of ionizing radiation which comprises first contacting the cells with a radiosensitizer of the present invention in a suitable carrier at a concentration effective to radiosensitize the cells for an amount of time effective to inhibit division of the cells, measuring the oxygenation of the cells, and then administering an effective cytotoxic dose of ionizing radiation to the cells.

The effectiveness of a method of the invention in treating a subject can be identified using well known methods. For example, the effectiveness of treatment can be identified by detecting prolonged survival of the subject, disappearance of the tumor, or a decreased rate of growth of an irradiated tumor as compared to the rate of growth prior to irradiation. In human cancer patients, such measurements generally are made using well known imaging methods such as magnetic resonance imaging, computerized axial tomography and X-rays. In addition, determination of the level of a tumor marker such as the detection of levels of circulating carcinoembryonic antigen (CEA) or prostate specific antigen or the like also can be used as an indication of the effectiveness of a treatment. Thus, the effectiveness of a method of the invention can be determined by measuring a decrease in the growth rate of a tumor or an appropriate change in the level of a circulating marker, the presence or relative level of which is indicative of cancer.

Considerable research has been directed to the identification of chemical agents that selectively increase the radiosensitivity of tumor cells, but not of normal cells. Cytokines, for example, are a class of molecules that, in some cases, also can act as radiosensitizing agents. While not being bound by theory, it is believed that the radiosensitizers of the present invention effect reoxygenation of a hypoxic region of a tumor by acting as an oxygen mimetic. Since normal tissue is well oxygenated, such a radiosensitizer can increase the sensitivity of the tumor cells, while having relatively less effect on the normal cells, thus effectively radiosensitizing the cancer cells.

Figure 3:
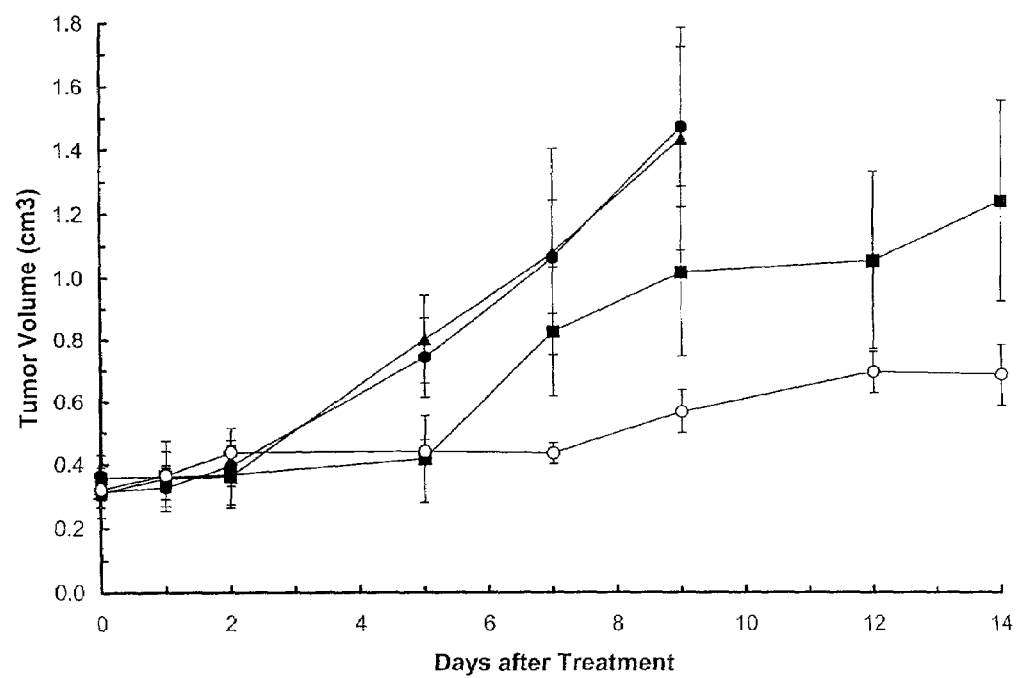
FIG. 3 shows tumor growth delay measurements in mice treated with RSR13 and/or radiation. Mice with tumors were injected i.p. with 200 mg/kg RSR13 and tumors were irradiated 30 min later at a dose of 10 Gy. A representative experiment is shown; error bars represent the±SEM of n=4 mice per treatment group. (filled circles), control, untreated; (filled triangles), RSR13 only (200 mg/kg); (filled squares), radiation only (10 Gy); (open circles), radiation+RSR13.
Figures 4A, 4B, 4C, 4D:
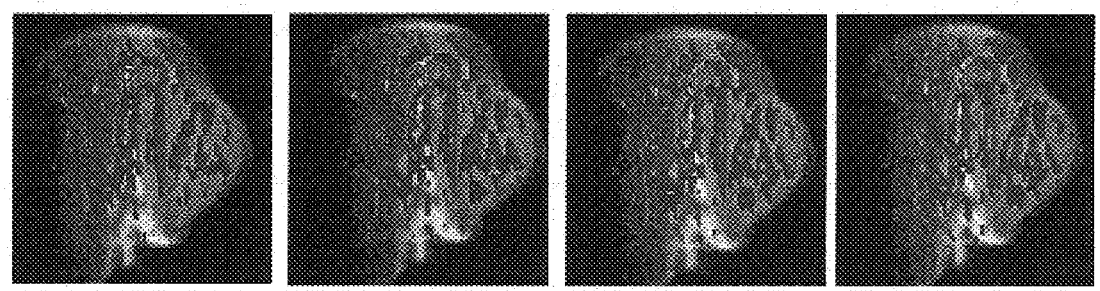
FIGS. 4A–G show color maps of percent T2* dependent gradient echo signal increase from baseline post-injection of 0 mg/kg RSR13 (control) at times 0 (FIG. 4A), 10 (FIG. 4B), 20 (FIG. 4C), 30 (FIG. 4D), 40 (FIG. 4E), 50 (FIG. 4F) and 60 (FIG. 4G) minutes. Color maps are superimposed over spin echo images of a single slice through the tumor.
Figures 4E, 4F, 4G:
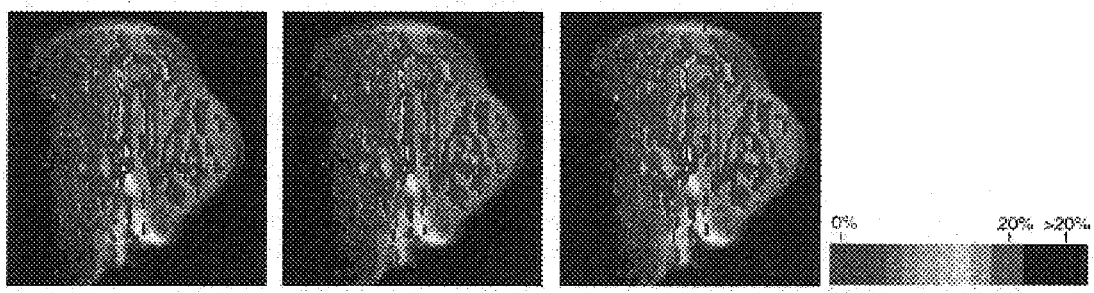
Figures 6A, 6B, 6C, 6D:
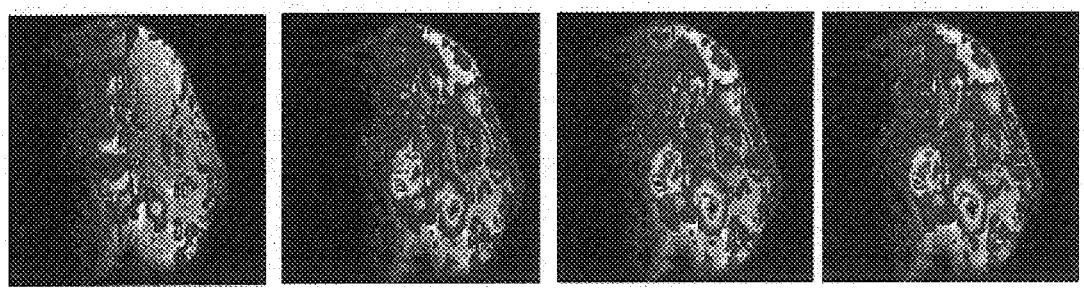
FIGS. 6A–G shows color maps of percent T2* dependent gradient echo signal increase from baseline post-injection of 300 mg/kg RSR13 at times 0 (FIG. 6A), 10 (FIG. 6B), 20 (FIG. 6C), 30 (FIG. 6D), 40 (FIG. 6E), 50 (FIG. 6F) and 60 (FIG. 6G) minutes. Color maps are superimposed over spin echo images of a single slice through the tumor.
Figures 6E, 6F, 6G:
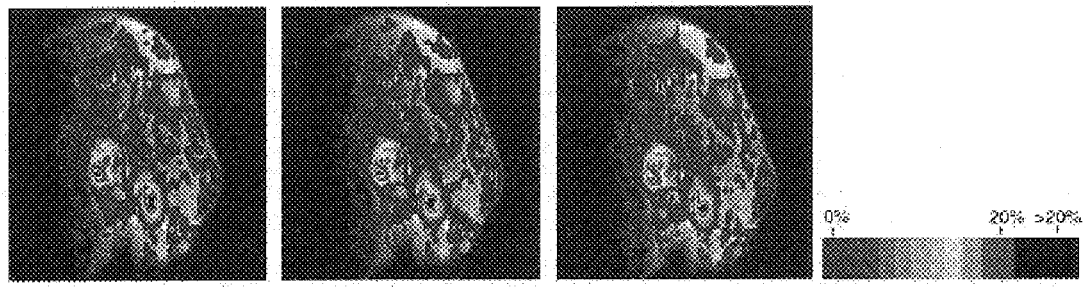
Figures 7A, 7B, 7C, 7D:
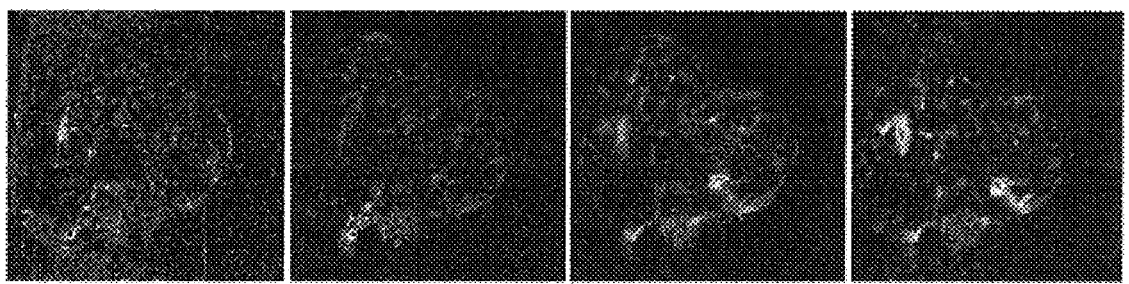
Figures 7E, 7F, 7G:
Figure 10:
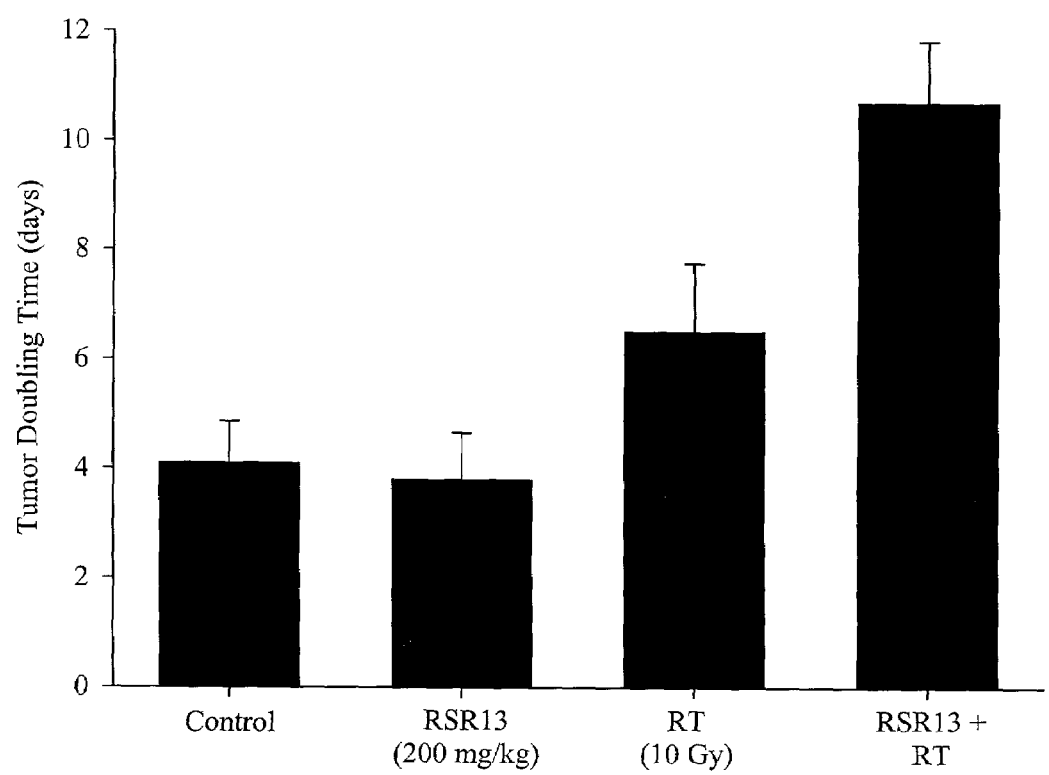
FIG. 10 shows tumor doubling times for each of the treatment groups described in FIG. 3.

The radiation enhancing properties of RSR13 on tumor growth delay at the optimum RSR13 dose level and timing strategy for tumor oxygenation have been determined using the BOLD MRI technique. Using RSR13 at a dose of 200 mg/kg and observing the MRI signal at 30 minutes after the dose was administered, radiation plus RSR13 experiments were performed (FIG. 3). Treatment with 200 mg/kg RSR13 alone did not affect tumor growth delay. Radiation alone (10 Gy) caused a growth delay of 2.4 days. The combination of RSR13 plus radiation given 30 min later yielded a growth delay of 6.6 days. An enhancement factor of 6.6/2.4=2.8 can be calculated using these tumor growth delay values. The tumor doubling times for each treatment group are compared in FIG. 10.

Results from these experiments demonstrate that BOLD MRI can be used as a noninvasive and spatially oriented method to quantify the effect of RSR13 on tumor oxygenation. RSR13 dose-dependently increases the MRI signal ration with a peak increase at 30 minutes after treatment, and administration of RSR13 30 minutes before irradiation increases the effectiveness of radiation significantly. Thus the enhancement of the effect of radiation is correlated with and increase in tumor oxygenation achieved by RSR13.

These results shows that radiation enhancement of tumor growth delay occurs using 200 mg/kg RSR13 with radiation given 30 min later. The enhancement ratios reported in these previous studies ranged from 1.3–1.8; however, these were calculated as dose modifying factors (which are generally smaller than an effects ratio), and these studies also involved fractionated radiotherapy.

These measurements of optimum RSR13 dose and optimum time of tumor oxygenation are in reasonable agreement with those of previous studies using $pO_2$ microelectrodes and $Hb-O_2$ affinity measurements. In one of these studies, the $pO_2$ at 50% hemoglobin saturation increased by a mean of 53% at 20–40 min after a 300 mg/kg RSR13 injection into mice.

Figure 8:
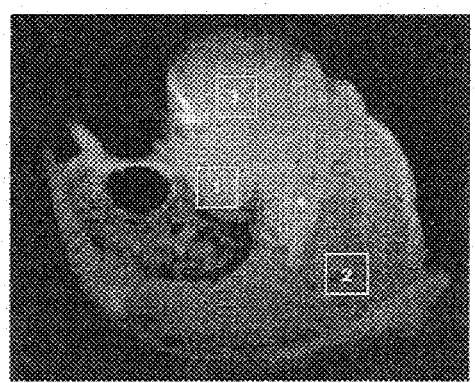
FIG. 8 shows (a) axial spin echo image of an athymic nude mouse with an H460 tumor growing in its flank. The regions of interest identified are [ROI 1] tumor, [ROI 2] normal tissue, and [ROI 3] necrotic tissue.
Figure 9:
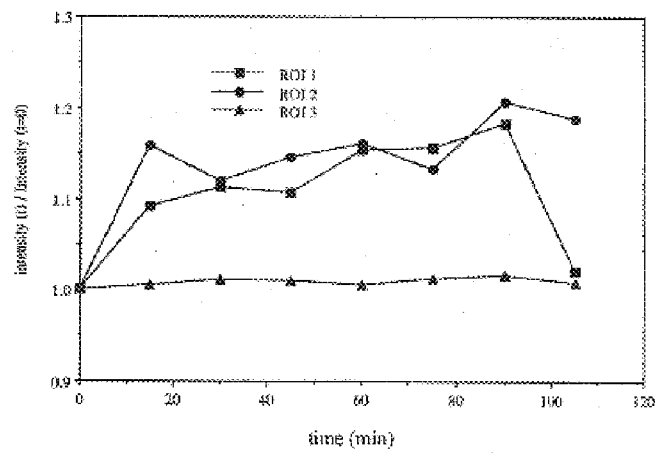
FIG. 9 shows a plot of signal in each ROI shown in FIG. 8, normalized to signal at time zero, as a function of time for approximately two hours after the time zero injection of RSR13. The nearly 20% increase in signal in tumor tissue reduces T1 and/or lengthens T2.

Experimental tumors in general are markedly hypoxic and the level of hypoxia varies with the tumor size. Subcutaneous lung tumors in mice such as Lewis lung carcinoma have been shown to have hypoxic fractions of at least 20%; this has been reported for A549 human xenografts. A comparison of various mouse tumor models has shown that there is very little histological difference between A549 and H460 non-small cell lung cancer xenografts. Thus a hypoxic fraction of about 20% might be expected for the H460 tumors. This expectation is supported by ultrasonic imaging and histological analysis of the H460 xenografts which revealed a necrotic tumor core, as shown in FIG. 8. When signal intensity is plotted as a function of time after injection of RSR13, a 20% increase in the signal in tumor tissue is seen, as shown in FIG. 9. This increase in signal intensity reduces T1 and/or lengthens T2.

The direction of the BOLD MRI signal intensity change (i.e. increase or decrease) can be controversial for several reasons, especially the definition of and interpretation of this signal change. Traditional BOLD MRI detects in the deoxyhemoglobin status of blood, which the venous blood signal predominating over all other factors. The level of paramagnetic deoxyhemoglobin in and near blood vessels affects $T^*2$ relaxation, which creates BOLD contrast. Since the mechanism of tissue oxygenation by RSR13 involves and increase in deoxyhemoglobin levels, a decrease in the BOLD MRI signal after RSR13 administration might be expected, depending upon the orientation of the signal processing parameters. In contrast, blood oxygenation (as opposed to tissue oxygenation) may cause increased oxygen saturation of hemoglobin and thus a decrease in deoxyhemoglobin levels.

To address these issues, the results presented herein have been compared to the of Al-Hallaq, et al., *Int. J. Radiat. Oncol. Biol. Phys.* (1998) 41:151–59, with attention to the details of their parameter definitions. Their initial studies showed that increases in the BOLD MRI signal (Δ%, which is proportional to T*2) were strongly correlated with increased tumor $pO_2$ levels in rodents (as measured using $pO_2$ microelectrodes). In a subsequent study, they showed that administration of various tumor-oxygenating agents causes an increase in the BOLD MRI parameter Δ%. See Al-Hallaq, *Int. J. Radiat. Oncol. Biol. Phys.* (2000) 47:481–88. However, they used the MR signal linewidth as an alternative parameter to report their data which decreases with increasing T*2. The MR signal intensity measured in this application is also proportional to T*2, based upon the parameters used. Since an increased signal is also observed with administration of a tumor-oxygenating agent, the studies of Al-Hallaq, et al. support the direction of the BOLD MRI signal we have measured in rodent tumors. It is also possible for the T1 effect, which is more strongly influenced by molecular oxygen than by deoxyhemoglobin, to compete with, and predominate over the T*2 effect. This phenomenon could cause an increase in the MRI signal with increasing tumor-oxygenation. Thus caution is necessary in the interpretation of BOLD MRI results involving different oxygenating agents, tissue types, and particularly in the orientation of MR parameter definitions when comparing the results of different studies.

EXAMPLES

Example 1

Mice and Tumor Inoculations

NCI-H460 human large cell lung carcinoma cells were obtained from the American Type Culture Collection (ATCC). H460 cells were cultured at 37° C., 5% $CO_2$ in RPMI 1640 medium (Gibco BRL, Gaithersburg, Md.)+10% fetal bovine serum (Gibco)+50 U/ml penicillin (Gibco)+50 μg/ml streptomycin (Gibco). Cells were routinely passaged using 0.05% trypsin-EDTA. Human NIH-H460 cells were used as a xenograft model in female athymic nude mice (nu/nu, 5–6 weeks old). Cells at 80% confluence were trypsinized, resuspended in growth medium, and counted. Cells were then centrifuged and resuspended in 37° C. PBS at $2 \times 10^7$ cells/ml. A suspension of $2 \times 10^6$ cells in a 0.1 ml volume was injected subcutaneously (s.c.) into the left posterior flank. Tumors were allowed to grow for 2 weeks (about 1 $cm^3$) before imaging, or for 7 days prior to treatment with RSR13 and radiation.

Example 2

RSR13 Treatment and BOLD MRI

Mice with tumors were anesthetized with 0.05 cc of a ketamine (100 mg/ml) and acepromezine (2.5 mg/0.25 ml) cocktail (induction anesthesia). A 24G angiocath, attached to a syringe with the appropriate amount of RSR13, was then placed and secured intraperitoneally (i.p.). Mice were placed in a pre-warmed anesthesia chamber and the surface coil was positioned over the tumor. The entire assembly was then placed into a Varian 4.7T small bore MR scanner. The anesthesia chamber was then infused with a mixture of 98.5% room air and 1.5% isoflurane (maintenance anesthesia) at a rate of 1.5 L/min throughout the experiment. After scout images were obtained to localize the tumor, serial gradient echo images were obtained at ten-minute intervals over a total of 60 minutes. RSR13 was supplied as a 20-mg/ml stock solution, which was diluted with sterile phosphate-buffered saline (PBS) prior to experiments to achieve the desired dose (mg/kg) per 0.31 injection volume. At the start of acquisition of the second image ("time 0"), a dose of RSR13 was injected i.p. RSR13 doses were administered in 0.3 ml volumes; control mice were given injections of saline. Preliminary experiments were performed to optimize the BOLD contrast, first by imaging mouse tumors without any drug, and then by administering different doses of RSR13. A dose of 200 mg/kg was then chosen for further studies. Parameters for BOLD-MRI scans were chosen to maximize sensitivity to oxygen dependent changes in the relaxation parameter T2*. The following MRI parameters were used: TR=520 ms, TE=27 ms, flip angle=45°, 18 signal averages, 230 μm spatial resolution, matrix=128×128, bandwidth=37.4 kHz, field of view=3×3 cm. Color maps indicating percent increase in signal relative to the baseline gradient echo image were created for each image. Color maps were overlaid on corresponding spin echo images for anatomic reference. After images were acquired, each individual tumor (at t=30 min.) was examined slice by slice, and a single slice which was most representative of the entire tumor was chosen. Within each representative slice, a 15×15-pixel regions of interest (ROI) was drawn around the area of maximum signal intensity (about 25% of the tumor slice area). The voxel size was 0.23 mm×0.23 mm×1 mm; thus the slice thickness was 1 mm. The same slice and ROI were then used to calculate the signal ratio corresponding to the other times for the same tumor. The following signal ratio was calculated: Intensity (t)/Intensity (t=0 min). Based on the signal parameters listed above, the MRI signal intesnsity is proportional to the MR relaxation time, T*2, which is linearly related to the level of oxygen saturation. See, e.g. Ogawa, et al., *Magn. Reson. Med.* 29:205–10 (1993). Images were analyzed in a blind fashion in the dose dependence studies, without knowledge of the drug doses used, to eliminate observer bias.

Example 3

Radiation Plus RSR13 Experiments

Tumors on the flanks of mice were irradiated using an Eldorado-8 $^{60}$Co γ irradiator (Neutron Products, Inc., Dickerson, Md.). The dose rate was 1.18 Gy/min, at an SSD of 56.5 cm. The non-tumor parts of mice were shielded using lead blocks. Mice were irradiated using restraining devices constructed from 50 ml conical polyethylene tubes taped to a Styrofoam pad. Mice were irradiated 30 min after administration of RSR13 (given by intraperitoneal injection).

Tumors were measured three times weekly in two perpendicular dimensions using Vernier calipers. Volumes were calculated using the formula: volume=0.4* $ab^2$ (a=long dimension, b=short dimension). Treatment began when tumors reached an average volume of about 0.3 $cm^3$. Growth delay time (GD) was calculated as the time for treated tumors to double in volume minus the time for control tumors to double in volume, with t=0 defined as the first day of treatment. Treatment groups consisted of either untreated control, radiation alone, RSR13 alone, or RSR13 plus radiation. Each treatment group contained four mice.

Example 4

Statistical Analyses

A paired t-test was applied to test the differences between baseline and follow-up time points. All tests of significance were two-sided, and differences were considered statistically significant when the P value was ≦0.05. SAS version 8.0 was used for all statistical analyses. A total of 4 mice were used for dose dependence studies, and eight mice for time dependence studies. Four mice per treatment group were used for the tumor growth delay.

Example 5

Imaging GBM

All MRI scans will be performed on a 1.5T MRI scanner. The protocol will consist of measurement of brain T2 relaxation times using a multi-echo (Carr-Purcell-Meiboom-Gill) multi-shot spin echo-planer imaging (EPI). Patients will receive RSR13 and BCNU (Carmustine). Patients will receive RSR13 at doses of 25 to 200 mg/kg administered over 30 minutes via a central venous access device. MRI scans will be obtained on one RSR13/BCNU dosing day. MRI imaging will be obtained prior to oxygen administration (baseline), prior to initiation of the RSR13 infusion, and then every 5 minutes until 1 hour post-start RSR13. SpO2 measurements will be recorded just prior to each MRI scan. The scan parameters will be matrix size 256×192 pixel, 3 mm slice thickness, 240 mm FOV, mufti-shot EPI (16 shots), TR=1 second. Within each multi-echo sequence, the T2 is determined from the intensity decay over TE-values of 25, 50, 75, and 100 msec. Scan time is 12 seconds per T2 value. The procedure will also be repeated with gradient echo imaging to measure T2*.

After the end of the imaging, the data will be stored on a magneto-optical disk. Processing of the experimental data will involve evaluation of the extent and intensity of T2/T2* changes as well as calculation of changes in oxygen concentration in abnormal and normal brain. T2 and T2* relaxation times will be measured at multiple regions of interest in the core of the tumor, in the tumor rim, in the peri-tumoral edema, and in the contralateral gray and white matter remote from the tumor site.

A 6% change in T2 or T2* signal (i.e. a 5 msec change from typical baseline of 80 msec) will be considered a change in T2 signal. T2 and T2* signal can be measured with accuracy of a few percent. A study testing the method of Van Zijl carried out at Johns Hopkins demonstrated measurement of T2 signal in humans at scan resolution 256×128 with an accuracy of +/−3.8% standard deviation (SD) per pixel. The model of Van Zijl will be used to estimate the effect of the observed changes in blood vessels and tissue. For example, in large vessels a change of this magnitude would typically represent an approximate 5% change in saturation. Changes of this order of magnitude are routinely and reliably detected in functional MRI imaging. T2* signal can be measured in humans with an error of less than +/−3% SD per pixel, and this measurement may be a snore sensitive although less quantitative measure of oxygenation changes.

Change in signal will be assessed in the following manner. Regions of interest will be identified within the brain tumor, in regions of normal brain in the contralateral hemisphere, and in peri-lesional edematous regions from conventional MRI images. For each patient, the baseline value will be calculated as the mean of the measurements in each region of interest from three baseline MRIs prior to infusion of RSR13 and the follow-up value as the mean of the measurements just prior to end of infusion, at end of infusion, and immediately following end of infusion (i.e., those readings taken when RSR13 effect would be maximal). In addition, the value of the signal utilized will be the average over the identified region of interest, and not an individual pixel. For each patient, the percent change will be calculated based on these mean scores. Therefore, there will only be one measurement of percent change for each patient in the region of interest for T2 and T2*. Measurement of T2* change, which is the more sensitive measure, will be the primary objective, although measurement of T2 change which can be quantitatively related to tumor oxygenation is a critical secondary endpoint.

What is claimed is:

1. A method for measuring a blood oxygen level-dependent magnetic resonance imaging signal, compnsing
   a) administering an effective amount of an allosteric effector compound capable of decreasing hemoglobin binding affinity for oxygen; and
   b) performing a blood oxygen level-dependent magnetic resonance imaging scan, whereby said blood oxygen level-dependent magnetic resonance imaging signal is measured, wherein the allosteric effector compound is a compound selected from the group consisting of:

a compound having the formula:

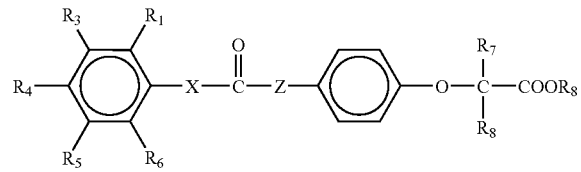

where $R_{1-5}$ may be hydrogen, halogen, or a substituted or unsubstituted $C_{1-3}$ alkyl group and may be the same or different, $R_{6-7}$ may each be hydrogen or methyl and may be the same or different, and $R_8$ may be hydrogen, a substituted or unsubstituted $C_{1-3}$ alkyl group, or a salt cation, and X and Z are $CH_2$, NH, or O;

a compound having the formula:

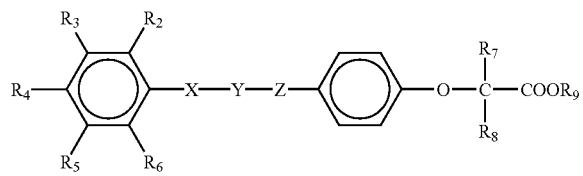

where X and Z may each be $CH_2$, CO, NH or O, and Y may be CO or NH, which the caveat that X, Y, and Z must all be different from each other, and $R_{2-6}$ can be the hydrogen, halogen, substituted or unsubstituted $C_{1-3}$ alkyl groups, and may be the same or different, $R_{7-8}$ can be hydrogens, methyls, ethyls, or alkyl groups in a ring connecting the two, and $R_9$ can be a hydrogen, lower alkyl, or salt cation;

a compound having the formula:

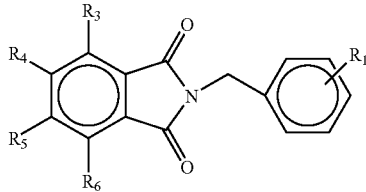

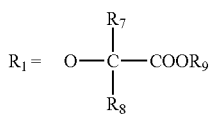

where $R_{3-6}$ can be the hydrogen, halogen, substituted or unsubstituted $C_{1-3}$ alkyl group, or a $C_{1-3}$ ether or ester, and these moieties may be the same or different, or alkyl moieties of an aromatic or aliphatic ring incorporating two of the $R_{3-6}$, $R_1$ can be connected to any position on the phenyl ring, and sites $R_{7-8}$ can be hydrogen, halogen, methyl, ethyl, and these moieties may be the same or different, or alkyl groups in a ring connecting the two, and $R_9$ can be a hydrogen, halogen, $C_{1-3}$ lower alkyl, or salt cation;

a compound having the formula:

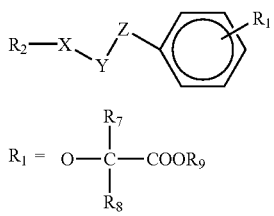

where $R_1$ can be connected to any position on the phenyl ring, and sites $R_{7-8}$ can be hydrogen, halogen, methyl, ethyl, and these moieties may be the same or different, or alkyl groups in a ring connecting the two, and $R_2$ is defined as a substituted or unsubstituted aromatic compound, a substituted or unsubstituted alkyl ring compound, or a substituted or unsubstituted phthalimide compound, X is a carboxyl, Y is a nitrogen, and $R_2$ completes the phthalimide compound by being bonded to both X and Y; and where X, Y, and Z, may either be $CH_2$, NH, O, or N, with the caveat that each are different from the other;

a compound having the formula:

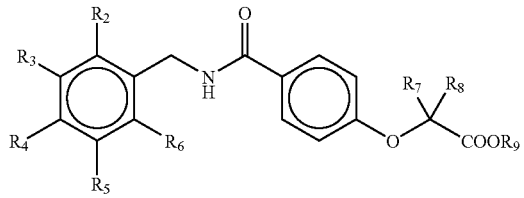

where $R_2$, $R_3$, $R_4$, $R_5$ and $R_6$ may be hydrogen, halogen, or alkyl groups and may be the same or different, $R_7$ and $R_8$ may be hydrogen or methyl groups and may be the same or different, and where the $R_9$ moiety is hydrogen or a salt cation;

a compound having the formula:

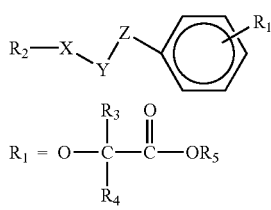

where $R_2$ is a substituted or unsubstituted aromatic compound, or a substituted or unsubstituted alkyl ring compound, or a substituted or unsubstituted phthalimide compound that incorporates X and Y, X is a carbonyl, Y is a nitrogen, and $R_2$ completes the phthalimide compound by being bonded to both X and Y, and where X, Y, and Z are $CH_2$, NH, S, $SO_2$, CO, O or N with the caveat that X, Y, and Z are each different from one another, and where $R_1$ can be connected to any position on the phenyl ring, and $R_3$ and $R_4$ are hydrogen, halogen, methyl, ethyl, propyl, isopropyl, neopentyl, butyl, or substituted or unsubstituted aryl groups and these moieties may be the same or different, or alkyl moieties as part of an aliphatic ring connecting $R_3$ and $R_4$, and $R_5$ is a hydrogen, halogen, $C_{1-3}$ lower alkyl, or a salt cation;

a compound having the formula:

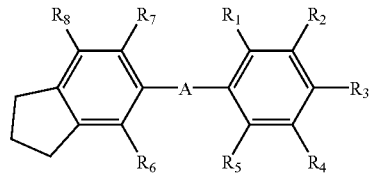

where A is a chemical bridge which includes two to four chemical moieties bonded together, the chemical moieties in A are selected from the group consisting of CO, O, S, $SO_2$ NH, $NR_9$ where $R_9$ is a $C_{1-6}$ alkyl group, $CH_2$, CH, and C, with the proviso that, except in the case where A contains two identical CH and C moieties positioned adjacent one another to form an alkene or alkyne, the chemical moieties in A are each different from one another, and at least one of $R_{1-5}$ is substituted with a compound having the chemical formula:

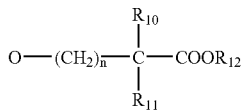

where n is zero to five, where $R_{10}$ and $R_{11}$ are selected from the group consisting of hydrogen, halogen, $C_{1-12}$ alkyl groups, carboxylic acids and esters, aromatic or heteroatomic groups, and these moieties may be the same or different, or alkyl moieties of part of an aliphatic ring connecting $R_{10}$ and $R_{11}$, and where $R_{12}$ is a hydrogen, halogen, salt cation, metal, or $C_{1-6}$ alkyl group, and wherein a remainder of the $R_{1-5}$ moieties and the $R_{6-8}$ moieties are selected from the group consisting of hydrogen, halogen, $C_{1-6}$ alkyl groups, $C_{1-6}$ ether or esters, aromatics and heteroaromatics, and alkyl moieties of an aliphatic ring connecting two sites on a phenyl group;

a compound having the formula:

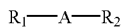

where $R_1$ and $R_2$ each are a substituted or unsubstituted aromatic or heteroaromatic compounds, or a substituted or unsubstituted alkyl or heteroalkyl ring compound, or a substituted or unsubstituted phthalimide compound, and where $R_1$ and $R_2$ may be the same or different, where A is a chemical bridge which includes three chemical moieties bonded together between $R_1$ and $R_2$, wherein the chemical moieties in A are selected from the group consisting of CO, O, S, $SO_2$, NH, $NR_3$ where $R_3$ is $C_{1-6}$ alkyl group, $NR_4$ where $R_4$ includes two carbonyls as part of a phthalimide compound formed with $R_1$ or $R_2$, $CH_2$, CH, and C, and where at least one of $R_1$ and $R_2$ is substituted with a compounds having the chemical formula:

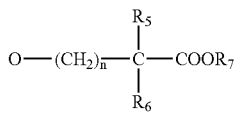

where n is zero to five, where $R_5$ and $R_6$ are selected from the group consisting of hydrogen, halogen, substituted or unsubstituted $C_{1-12}$ alkyl groups, carboxylic acid and ester groups, substituted or unsubstituted aromatic or heteroaromatic groups, and these moieties may be the same or different, or alkyl moieties of part of an aliphatic ring connecting $R_5$ and $R_6$, and where $R_7$ is a hydrogen, halogen, salt cation, metal, or substituted or unsubstituted $C_{1-6}$ alkyl group;

a compound having the formula:

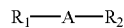

where $R_1$ and $R_2$ each are a substituted or unsubstituted aromatic or heteroaromatic compound, or substituted or unsubstituted alkyl or heteroalkyl ring compound, or a substituted or unsubstituted phthalimide compound, and where $R_1$ and $R_2$ may be the same or different, where A is a chemical bridge which includes two to four chemical moieties bonded together between $R_1$ and $R_2$, wherein said chemical moieties in A are selected from the group consisting of CO, O, S, $SO_2$, NH, $NR_3$ where $R_3$ is a $C_{1-6}$ alkyl group, $NR_4$ where $R_4$ includes two carbonyls as part of a phthalimide compound formed with $R_1$ or $R_2$, $CH_2$, CH, and C, with the caveat that, except in the case where A contains two identical CH and C moieties positioned adjacent one another to form an alkene or alkyne, the chemical moieties in A are each different from one another, and wherein at least one of $R_1$ or $R_2$ is substituted with a compound having the chemical formula:

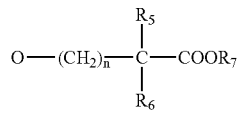

where n is zero to five, where $R_5$ and $R_6$ are selected from the group consisting of hydrogen, halogen, substituted or unsubstituted $C_{1-2}$ alkyl groups, carboxylic acid and ester, substituted or unsubstituted aromatic or heteroaromatic groups, and these moieties may be the same or different, or alkyl moieties of part of an aliphatic ring connecting $R_5$ and $R_6$, and where $R_7$ is a hydrogen, halogen, salt cation, metal, or substituted or unsubstituted $C_{1-6}$ alkyl group; and a compound having the formula:

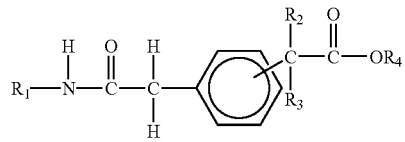

where $R_1$ is selected from the group consisting of optionally substituted phenyl, adamantyl, napthyl, and indanyl, $R_{2-3}$ are alkyl moieties of a $C_{3-6}$ alkyl ring connecting $R_2$ and $R_3$, and $R_4$ is a hydrogen, a monovalent salt cation, or a $C_{1-3}$ lower alkyl.

2. The method of claim 1, wherein the allosteric effector compound is administered at a dose of 100–300 mg/kg.

3. The method of claim 1, wherein the allosteric effector compound is 2-[4-(((3,5-dimethylanilino)carbonyl)methyl) phenoxy]-2-methylpropionic acid, or a physiologically acceptable salt thereof.

4. The method of claim 3, wherein the allosteric effector compound is administered at a dose of 100–300 mg/kg.

5. The method of claim 3, wherein the allosteric effector compound is administered at a dose of 200 mg/kg.

6. A method of measuring tumor oxygenation, comprising
a) administering an effective amount of an allosteric effector compound capable of decreasing hemoglobin binding affinity for oxygen; and
b) performing a blood oxygen level-dependent magnetic resonance imaging scan, whereby oxygenation of the tumor is measured, wherein the allosteric effector compound is a compound selected from the group consisting of:
a compound having the formula:

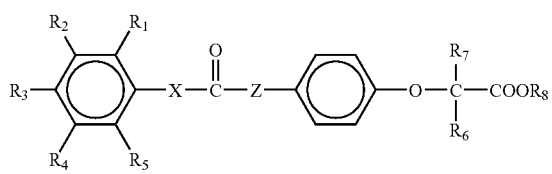

where $R_{1-5}$ may be hydrogen, halogen, or a substituted or unsubstituted $C_{1-3}$ alkyl group and may be the same or different, $R_{6-7}$ may each be hydrogen or methyl and may be the same or different, and $R_8$ may be hydrogen, a substituted or unsubstituted $C_{1-3}$ alkyl group, or a salt cation, and X and Z are $CH_2$, NH, or O;

a compound having the formula:

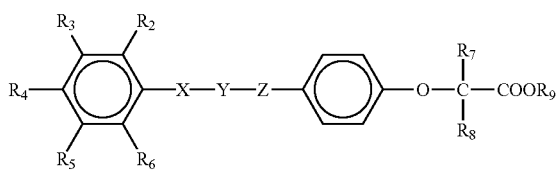

where X and Z may each be $CH_2$, CO, NH or O, and Y may be CO or NH, which the caveat that X, Y, and Z must all be different from each other, and $R_{2-6}$ can be the hydrogen, halogen, substituted or unsubstituted $C_{1-3}$ alkyl groups, and may be the same or different, $R_{7-8}$ can be hydrogens, methyls, ethyls, or alkyl groups in a ring connecting the two, and $R_9$ can be a hydrogen, lower alkyl, or salt cation;
a compound having the formula:

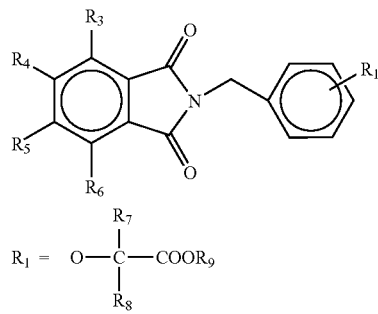

where $R_{3-6}$ can be the hydrogen, halogen, substituted or unsubstituted $C_{1-3}$ alkyl group, or a $C_{1-3}$ ether or ester, and these moieties may be the same or different, or alkyl moieties of an aromatic or aliphatic ring incorporating two of the $R_{3-6}$, $R_1$ can be connected to any position on the phenyl ring, and sites $R_{7-8}$ can be hydrogen, halogen, methyl, ethyl, and these moieties may be the same or different, or alkyl groups in a ring connecting the two, and $R_9$ can be a hydrogen, halogen, $C_{1-3}$ lower alkyl, or salt cation;

a compound having the formula:

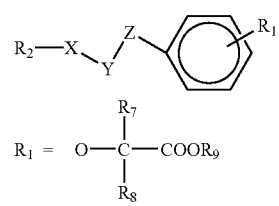

where $R_1$ can be connected to any position on the phenyl ring, and sites $R_{7-8}$ can be hydrogen, halogen, methyl, ethyl, and these moieties may be the same or different, or alkyl groups in a ring connecting the two, and $R_2$ is defined as a substituted or unsubstituted aromatic compound, a substituted or unsubstituted alkyl ring compound, or a substituted or unsubstituted phthalimide compound, X is a carboxyl, Y is a nitrogen, and $R_2$ completes the phthalimide compound by being bonded to both X and Y; and where X, Y, and Z, may either be $CH_2$, NH, O, or N, with the caveat that each are different from the other;

a compound having the formula:

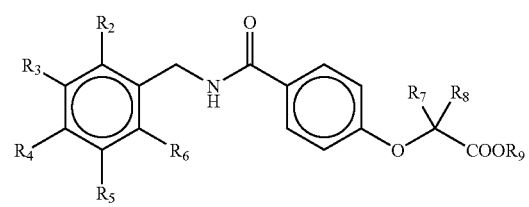

where $R_2$, $R_3$, $R_4$, $R_5$ and $R_6$ may be hydrogen, halogen, or alkyl groups and may be the same or different, $R_7$ and $R_8$ may be hydrogen or methyl groups and may be the same or different, and where the $R_9$ moiety is hydrogen or a salt cation;

a compound having the formula:

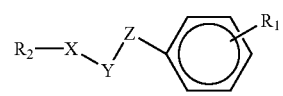

-continued

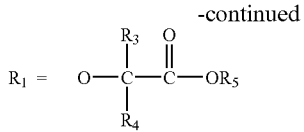

where $R_2$ is a substituted or unsubstituted aromatic compound, or a substituted or unsubstituted alkyl ring compound, or a substituted or unsubstituted phthalimide compound that incorporates X and Y,
X is a carbonyl,
Y is a nitrogen, and
$R_2$ completes the phthalimide compound by being bonded to both X and Y, and where X, Y, and Z are $CH_2$, NH, S, $SO_2$, CO, O or N with the caveat that X, Y, and Z are each different from one another, and
where $R_1$ can be connected to any position on the phenyl ring, and
$R_3$ and $R_4$ are hydrogen, halogen, methyl, ethyl, propyl, isopropyl, neopentyl, butyl, or substituted or unsubstituted aryl groups and these moieties may be the same or different, or alkyl moieties as part of an aliphatic ring connecting $R_3$ and $R_4$, and
$R_5$ is a hydrogen, halogen, $C_{1-3}$ lower alkyl, or a salt cation;
a compound having the formula:

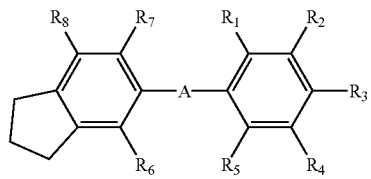

where A is a chemical bridge which includes two to four chemical moieties bonded together,
the chemical moieties in A are selected from the group consisting of CO, O, S, $SO_2$, NH, $NR_9$ where $R_9$ is a $C_{1-6}$ alkyl group, $CH_2$, CH, and C, with the proviso that, except in the case where A contains two identical CH and C moieties positioned adjacent one another to form an alkene or alkyne, the chemical moieties in A are each different from one another, and
at least one of $R_{1-5}$ is substituted with a compound having the chemical formula:

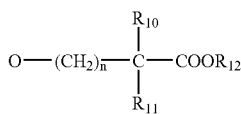

where n is zero to five,
where $R_{10}$ and $R_{11}$ are selected from the group consisting of hydrogen, halogen, $C_{1-12}$ alkyl groups, carboxylic acids and esters, aromatic or heteroatomic groups, and these moieties may be the same or different, or alkyl moieties of part of an aliphatic ring connecting $R_{10}$ and $R_{11}$, and where $R_{12}$ is a hydrogen, halogen, salt cation, metal, or $C_{1-6}$ alkyl group, and wherein a remainder of the $R_{1-5}$ moieties and the $R_{6-8}$ moieties are selected from the group consisting of hydrogen, halogen, $C_{1-6}$ alkyl groups, $C_{1-6}$ ether or esters, aromatics and heteroaromatics, and alkyl moieties of an aliphatic ring connecting two sites on a phenyl group;
a compound having the formula:

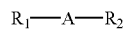

where $R_1$ and $R_2$ each are a substituted or unsubstituted aromatic or heteroaromatic compounds, or a substituted or unsubstituted alkyl or heteroalkyl ring compound, or a substituted or unsubstituted phthalimide compound, and
where $R_1$ and $R_2$ may be the same or different,
where A is a chemical bridge which includes three chemical moieties bonded together between $R_1$ and $R_2$,
wherein the chemical moieties in A are selected from the group consisting of CO, O, S, $SO_2$, NH, $NR_3$ where $R_3$ is $C_{1-6}$ alkyl group, $NR_4$ where $R_4$ includes two carbonyls as part of a phthalimide compound formed with $R_1$ or $R_2$, $CH_2$, CH, and C, and
where at least one of $R_1$ and $R_2$ is substituted with a compounds having the chemical formula:

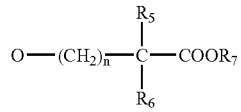

where n is zero to five, where $R_5$ and $R_6$ are selected from the group consisting of hydrogen, halogen, substituted or unsubstituted $C_{1-12}$ alkyl groups, carboxylic acid and ester groups, substituted or unsubstituted aromatic or heteroaromatic groups, and these moieties may be the same or different, or alkyl moieties of part of an aliphatic ring connecting $R_5$ and $R_6$, and
where $R_7$ is a hydrogen, halogen, salt cation, metal, or substituted or unsubstituted $C_{1-6}$ alkyl group;
a compound having the formula:

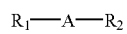

where $R_1$ and $R_2$ each are a substituted or unsubstituted aromatic or heteroaromatic compound, or substituted or unsubstituted alkyl or heteroalkyl ring compound, or a substituted or unsubstituted phthalimide compound, and
where $R_1$ and $R_2$ may be the same or different,
where A is a chemical bridge which includes two to four chemical moieties bonded together between $R_1$ and $R_2$,
wherein said chemical moieties in A are selected from the group consisting of CO, O, S, $SO_2$, NH, $NR_3$ where $R_3$ is a $C_{1-6}$ alkyl group, $NR_4$ where $R_4$ includes two carbonyls as part of a phthalimide compound formed with $R_1$ or $R_2$, $CH_2$, CH, and C, with the caveat that, except in the case where A contains two identical CH and C moieties positioned adjacent one another to form an alkene or alkyne, the chemical moieties in A are each different from one another, and wherein at least one of $R_1$ or $R_2$ is substituted with a compound having the chemical formula:

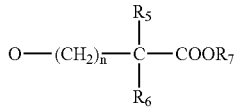

where n is zero to five, where $R_5$ and $R_6$ are selected from the group consisting of hydrogen, halogen, substituted or unsubstituted $C_{1-2}$ alkyl groups, carboxylic acid and ester, substituted or unsubstituted aromatic or heteroaromatic groups, and these moieties may be the same or different, or alkyl moieties of part of an aliphatic ring connecting $R_5$ and $R_6$, and where $R_7$ is a hydrogen, halogen, salt cation, metal, or substituted or unsubstituted $C_{1-6}$ alkyl group; and a compound having the formula:

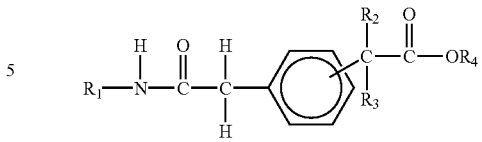

where $R_1$ is selected from the group consisting of optionally substituted phenyl, adamantyl, napthyl, and indanyl, $R_{2-3}$ are alkyl moieties of a $C_{3-6}$ alkyl ring connecting $R_2$ and $R_3$, and $R_4$ is a hydrogen, a monovalent salt cation, or a $C_{1-3}$ lower alkyl.

7. The method of claim 6, wherein the allosteric effector compound is administered at a dose of 100–300 mg/kg.

8. The method of claim 6, wherein the oxygenation of the tumor is measured quantitatively.

9. The method of claim 6, wherein the allosteric effector compound is 2-[4-(((3,5-dimethylanilino)carbonyl)methyl)phenoxy]-2-methylpropionic acid, or a physiologically acceptable salt thereof.

10. The method of claim 9, wherein the allosteric effector compound is administered at a dose of 100–300 mg/kg.

11. The method of claim 9, wherein the allosteric effector compound is administered at a dose of 200 mg/kg.

* * * * *